United States Patent
Afonso et al.

(10) Patent No.: US 9,204,927 B2
(45) Date of Patent: Dec. 8, 2015

(54) SYSTEM AND METHOD FOR PRESENTING INFORMATION REPRESENTATIVE OF LESION FORMATION IN TISSUE DURING AN ABLATION PROCEDURE

(75) Inventors: Valtino X. Afonso, Oakdale, MN (US); Lubomir V. Dragnev, St. Louis, MO (US); Sarah E. Cumming, Wake Forest, MO (US); Yitzhak I. Shai, Springfield, NJ (US); Saurav Paul, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 634 days.

(21) Appl. No.: 12/964,910

(22) Filed: Dec. 10, 2010
(Under 37 CFR 1.47)

(65) Prior Publication Data
US 2012/0029504 A1    Feb. 2, 2012

Related U.S. Application Data

(63) Continuation-in-part of application No. 12/946,941, filed on Nov. 16, 2010, now Pat. No. 8,603,084, which is a continuation-in-part of application No. 12/622,488, filed on Nov. 20, 2009, now Pat. No. 8,403,925.

(60) Provisional application No. 61/177,876, filed on May 13, 2009.

(51) Int. Cl.
- *A61B 18/10* (2006.01)
- *A61B 18/14* (2006.01)
(Continued)

(52) U.S. Cl.
CPC ........ *A61B 18/1492* (2013.01); *A61B 5/0402* (2013.01); *A61B 5/042* (2013.01);
(Continued)

(58) Field of Classification Search
USPC ................................ 606/27, 34, 41
See application file for complete search history.

(56) References Cited

U.S. PATENT DOCUMENTS

| 2,184,511 | A | 12/1939 | Bagno et al. |
| 3,316,896 | A | 5/1967 | Thomasset |

(Continued)

FOREIGN PATENT DOCUMENTS

| EP | 1472976 | 11/2004 |
| EP | 1586281 | 4/2009 |

(Continued)

OTHER PUBLICATIONS

"International Search Report & Written Opinion", PCT/US2011/047235 Dec. 14, 2011.

(Continued)

*Primary Examiner* — Michael Peffley
*Assistant Examiner* — Daniel Fowler
(74) *Attorney, Agent, or Firm* — Dykema Gossett PLLC

(57) ABSTRACT

A method and system for presenting information representative of lesion formation is provided. The system comprises an electronic control unit (ECU). The ECU is configured to acquire a value for an ablation description parameter and/or a position signal metric, wherein the value corresponds to a location in the tissue. The ECU is further configured to evaluate the value, assign it a visual indicator of a visualization scheme associated with the parameter/metric corresponding to the value, and generate a marker comprising the visual indicator such that the marker is indicative of the acquired value. The method comprises acquiring a value for the parameter/metric, and evaluating the value. The method further includes assigning a visual indicator of a visualization scheme associated with the parameter/metric corresponding to the value, and generating a marker comprising the visual indicator.

26 Claims, 14 Drawing Sheets

(51) Int. Cl.
  *A61B 5/0402* (2006.01)
  *A61B 5/042* (2006.01)
  *A61B 18/12* (2006.01)
  *A61B 18/24* (2006.01)
  *A61B 19/00* (2006.01)
  *A61B 17/00* (2006.01)
  *A61B 18/00* (2006.01)
  *A61B 18/02* (2006.01)
  *A61N 7/02* (2006.01)
  *A61B 5/00* (2006.01)

(52) U.S. Cl.
  CPC .......... *A61B 5/7203* (2013.01); *A61B 18/1233* (2013.01); *A61B 18/14* (2013.01); *A61B 18/24* (2013.01); *A61B 19/56* (2013.01); *A61B 2017/00128* (2013.01); *A61B 2018/00178* (2013.01); *A61B 2018/00351* (2013.01); *A61B 2018/00577* (2013.01); *A61B 2018/00702* (2013.01); *A61B 2018/00714* (2013.01); *A61B 2018/00738* (2013.01); *A61B 2018/00779* (2013.01); *A61B 2018/00875* (2013.01); *A61B 2018/00892* (2013.01); *A61B 2018/0212* (2013.01); *A61B 2018/0262* (2013.01); *A61B 2019/2211* (2013.01); *A61B 2019/465* (2013.01); *A61B 2019/504* (2013.01); *A61B 2019/5246* (2013.01); *A61B 2019/5251* (2013.01); *A61B 2218/002* (2013.01); *A61N 7/022* (2013.01)

(56) References Cited

U.S. PATENT DOCUMENTS

| | | | |
|---|---|---|---|
| 3,949,736 | A | 4/1976 | Vrana et al. |
| 4,641,649 | A | 2/1987 | Walinsky et al. |
| 5,230,349 | A | 7/1993 | Langberg |
| 5,257,635 | A | 11/1993 | Langberg |
| 5,297,549 | A | 3/1994 | Beatty et al. |
| 5,311,866 | A | 5/1994 | Kagan et al. |
| 5,341,807 | A | 8/1994 | Nardella |
| 5,366,896 | A | 11/1994 | Margrey et al. |
| 5,423,808 | A | 6/1995 | Edwards et al. |
| 5,429,131 | A | 7/1995 | Scheinman |
| 5,447,529 | A | 9/1995 | Marchlinski et al. |
| 5,546,940 | A | 8/1996 | Panescu et al. |
| 5,562,721 | A | 10/1996 | Marchlinski et al. |
| 5,582,609 | A | 12/1996 | Swanson |
| 5,588,432 | A | 12/1996 | Crowley |
| 5,630,034 | A | 5/1997 | Oikawa |
| 5,657,755 | A | 8/1997 | Desai |
| 5,659,624 | A | 8/1997 | Fazzari |
| 5,673,704 | A | 10/1997 | Marchlinski et al. |
| 5,688,267 | A | 11/1997 | Panescu |
| 5,697,377 | A | 12/1997 | Wittkampf |
| 5,702,386 | A | 12/1997 | Stern et al. |
| 5,718,241 | A | 2/1998 | Ben-Haim et al. |
| 5,722,402 | A | 3/1998 | Swanson |
| 5,730,127 | A | 3/1998 | Avitall |
| 5,759,159 | A | 6/1998 | Masreliez |
| 5,782,900 | A | 7/1998 | de la Rama |
| 5,800,350 | A | 9/1998 | Coppleson |
| 5,810,742 | A | 9/1998 | Pearlman |
| 5,814,043 | A | 9/1998 | Shapeton |
| 5,836,943 | A | 11/1998 | Miller, III |
| 5,836,990 | A | 11/1998 | Li |
| 5,837,001 | A | 11/1998 | Mackey |
| 5,846,238 | A | 12/1998 | Jackson et al. |
| 5,904,709 | A | 5/1999 | Arndt |
| 5,944,022 | A | 8/1999 | Nardella et al. |
| 5,954,665 | A | 9/1999 | Ben-Haim |
| 6,001,093 | A | 12/1999 | Swanson |
| 6,019,757 | A | 2/2000 | Scheldrup |
| 6,026,323 | A | 2/2000 | Skladnev |
| 6,035,341 | A | 3/2000 | Nunally |
| 6,063,078 | A | 5/2000 | Wittkampf |
| 6,129,669 | A | 10/2000 | Panescu et al. |
| 6,171,304 | B1 | 1/2001 | Netherly |
| 6,179,824 | B1 | 1/2001 | Eggers et al. |
| 6,206,874 | B1 | 3/2001 | Ubby |
| 6,217,574 | B1 | 4/2001 | Webster |
| 6,217,576 | B1 | 4/2001 | Tu |
| 6,221,070 | B1 | 4/2001 | Tu et al. |
| 6,226,542 | B1 | 5/2001 | Reisfeld |
| 6,233,476 | B1 | 5/2001 | Strommer et al. |
| 6,246,896 | B1 | 6/2001 | Dumoulin |
| 6,256,540 | B1 | 7/2001 | Panescu et al. |
| 6,322,558 | B1 | 11/2001 | Taylor et al. |
| 6,337,994 | B1 | 1/2002 | Stoianovici |
| 6,391,024 | B1 | 5/2002 | Sun et al. |
| 6,423,057 | B1 | 7/2002 | He et al. |
| 6,427,089 | B1 | 7/2002 | Knowlton |
| 6,443,894 | B1 | 9/2002 | Sumanaweera et al. |
| 6,445,952 | B1 | 9/2002 | Manrodt et al. |
| 6,456,864 | B1 | 9/2002 | Swanson et al. |
| 6,471,693 | B1 | 10/2002 | Carroll et al. |
| 6,475,215 | B1 | 11/2002 | Tanrisever |
| 6,490,474 | B1 | 12/2002 | Willis et al. |
| 6,498,944 | B1 | 12/2002 | Ben-Haim et al. |
| 6,507,751 | B2 | 1/2003 | Blume et al. |
| 6,511,478 | B1 | 1/2003 | Burnside et al. |
| 6,546,270 | B1* | 4/2003 | Goldin et al. ................ 600/374 |
| 6,558,382 | B2 | 5/2003 | Jahns et al. |
| 6,569,160 | B1 | 5/2003 | Goldin |
| 6,575,969 | B1* | 6/2003 | Rittman et al. ............... 606/41 |
| 6,605,082 | B2 | 8/2003 | Hareyama et al. |
| 6,652,518 | B2 | 11/2003 | Wellman et al. |
| 6,663,622 | B1 | 12/2003 | Foley et al. |
| 6,683,280 | B1 | 1/2004 | Wofford |
| 6,690,963 | B2 | 2/2004 | Ben-Haim et al. |
| 6,696,844 | B2 | 2/2004 | Wong et al. |
| 6,712,074 | B2 | 3/2004 | Edwards et al. |
| 6,743,225 | B2 | 6/2004 | Sanchez |
| 6,755,790 | B2 | 6/2004 | Stewart |
| 6,780,182 | B2 | 8/2004 | Bowman |
| 6,788,967 | B2 | 9/2004 | Ben-Haim et al. |
| 6,813,515 | B2 | 11/2004 | Hashimshony |
| 6,840,938 | B1 | 1/2005 | Morley et al. |
| 6,917,834 | B2 | 7/2005 | Koblish et al. |
| 6,918,876 | B1* | 7/2005 | Kamiyama ................ 600/447 |
| 6,926,669 | B1 | 8/2005 | Stewart |
| 6,936,047 | B2 | 8/2005 | Nasab |
| 6,950,689 | B1 | 9/2005 | Willis et al. |
| 6,964,867 | B2 | 11/2005 | Downs |
| 6,965,795 | B2 | 11/2005 | Rock |
| 6,993,384 | B2 | 1/2006 | Bradley et al. |
| 7,041,095 | B2 | 5/2006 | Wang et al. |
| 7,041,096 | B2 | 5/2006 | Malis |
| 7,106,043 | B1 | 9/2006 | Da Silva |
| 7,197,354 | B2 | 3/2007 | Sobe |
| 7,248,032 | B1 | 7/2007 | Hular |
| 7,263,395 | B2 | 8/2007 | Chan et al. |
| 7,263,397 | B2 | 8/2007 | Hauck et al. |
| 7,386,339 | B2 | 6/2008 | Strommer et al. |
| 7,497,858 | B2 | 3/2009 | Chapelon et al. |
| 7,499,745 | B2 | 3/2009 | Littrup |
| 7,536,218 | B2 | 5/2009 | Govari et al. |
| 7,565,613 | B2 | 7/2009 | Forney |
| 7,610,078 | B2 | 10/2009 | Willis |
| 7,633,502 | B2 | 12/2009 | Willis et al. |
| 7,671,871 | B2 | 3/2010 | Gonsalves |
| 7,776,034 | B2 | 8/2010 | Kampa |
| 7,819,870 | B2 | 10/2010 | Thao |
| 7,865,236 | B2 | 1/2011 | Cory |
| 7,904,174 | B2 | 3/2011 | Hammill et al. |
| 7,953,495 | B2 | 5/2011 | Sommer et al. |
| 8,075,498 | B2 | 12/2011 | Leo et al. |
| 2001/0034501 | A1 | 10/2001 | Tom |
| 2001/0039413 | A1 | 11/2001 | Bowe |
| 2001/0047129 | A1 | 11/2001 | Hall |
| 2001/0051774 | A1 | 12/2001 | Littrup et al. |
| 2002/0022836 | A1 | 2/2002 | Goble |
| 2002/0049375 | A1 | 4/2002 | Strommer et al. |

(56) References Cited

U.S. PATENT DOCUMENTS

| | | |
|---|---|---|
| 2002/0068931 A1 | 6/2002 | Wong |
| 2002/0072686 A1 | 6/2002 | Hoey et al. |
| 2002/0077627 A1 | 6/2002 | Johnson et al. |
| 2002/0120188 A1 | 8/2002 | Brock et al. |
| 2002/0123749 A1 | 9/2002 | Jain |
| 2002/0177847 A1 | 11/2002 | Long |
| 2003/0004587 A1 | 1/2003 | Raymond et al. |
| 2003/0028183 A1 | 2/2003 | Sanchez et al. |
| 2003/0045871 A1 | 3/2003 | Jain et al. |
| 2003/0060696 A1 | 3/2003 | Skladnev et al. |
| 2003/0065364 A1 | 4/2003 | Wellman et al. |
| 2003/0093067 A1 | 5/2003 | Panescu et al. |
| 2003/0093069 A1 | 5/2003 | Panescu et al. |
| 2003/0100823 A1 | 5/2003 | Kipke |
| 2003/0109871 A1 | 6/2003 | Johnson et al. |
| 2003/0130711 A1 | 7/2003 | Pearson et al. |
| 2003/0187430 A1 | 10/2003 | Vorisek |
| 2004/0006337 A1 | 1/2004 | Nasab et al. |
| 2004/0030258 A1 | 2/2004 | Williams et al. |
| 2004/0044292 A1 | 3/2004 | Yasushi et al. |
| 2004/0078036 A1* | 4/2004 | Keidar .................. 606/41 |
| 2004/0078058 A1 | 4/2004 | Holmstrom |
| 2004/0082946 A1 | 4/2004 | Malis et al. |
| 2004/0087975 A1 | 5/2004 | Lucatero |
| 2004/0097806 A1 | 5/2004 | Hunter |
| 2004/0147920 A1 | 7/2004 | Keidar |
| 2004/0181165 A1 | 9/2004 | Hoey et al. |
| 2004/0243018 A1 | 12/2004 | Organ |
| 2004/0243181 A1 | 12/2004 | Conrad |
| 2004/0267252 A1 | 12/2004 | Washington |
| 2005/0010263 A1 | 1/2005 | Schauerte |
| 2005/0054944 A1 | 3/2005 | Nakada |
| 2005/0065507 A1 | 3/2005 | Hartley |
| 2005/0222554 A1 | 10/2005 | Wallace |
| 2006/0015033 A1 | 1/2006 | Blakley et al. |
| 2006/0085079 A1 | 4/2006 | Cory et al. |
| 2006/0173251 A1 | 8/2006 | Govari |
| 2006/0200049 A1 | 9/2006 | Leo et al. |
| 2006/0235286 A1 | 10/2006 | Stone |
| 2007/0016006 A1 | 1/2007 | Shachar |
| 2007/0055142 A1 | 3/2007 | Webler |
| 2007/0073179 A1 | 3/2007 | Afonso et al. |
| 2007/0083193 A1 | 4/2007 | Werneth et al. |
| 2007/0100332 A1 | 5/2007 | Paul et al. |
| 2007/0106289 A1 | 5/2007 | O'Sullivan |
| 2007/0123764 A1 | 5/2007 | Thao et al. |
| 2007/0161915 A1 | 7/2007 | Desai |
| 2007/0225558 A1 | 9/2007 | Hauck et al. |
| 2007/0225593 A1 | 9/2007 | Porath |
| 2007/0244479 A1 | 10/2007 | Beatty et al. |
| 2007/0255162 A1 | 11/2007 | Abboud et al. |
| 2008/0091193 A1 | 4/2008 | Kauphusman |
| 2008/0097220 A1 | 4/2008 | Lieber |
| 2008/0097422 A1 | 4/2008 | Edwards et al. |
| 2008/0132890 A1 | 6/2008 | Woloszko |
| 2008/0183071 A1 | 7/2008 | Strommer et al. |
| 2008/0183189 A1* | 7/2008 | Teichman et al. .............. 606/130 |
| 2008/0221440 A1* | 9/2008 | Iddan et al. .................... 600/424 |
| 2008/0234564 A1 | 9/2008 | Beatty et al. |
| 2008/0249536 A1 | 10/2008 | Stahler |
| 2008/0275465 A1 | 11/2008 | Paul et al. |
| 2008/0288023 A1 | 11/2008 | John |
| 2008/0288038 A1 | 11/2008 | Paul et al. |
| 2008/0300589 A1 | 12/2008 | Paul et al. |
| 2008/0312713 A1 | 12/2008 | Wilfley |
| 2009/0012533 A1 | 1/2009 | Barbagli |
| 2009/0036794 A1 | 2/2009 | Stubhaug et al. |
| 2009/0163904 A1 | 6/2009 | Miller et al. |
| 2009/0171235 A1 | 7/2009 | Schneider et al. |
| 2009/0171345 A1 | 7/2009 | Miller et al. |
| 2009/0177111 A1 | 7/2009 | Miller et al. |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman et al. |
| 2009/0248042 A1 | 10/2009 | Kirschenman |
| 2009/0275827 A1 | 11/2009 | Aiken et al. |
| 2009/0276002 A1 | 11/2009 | Sommer |
| 2009/0306655 A1 | 12/2009 | Stangenes |
| 2010/0069921 A1 | 3/2010 | Miller et al. |
| 2010/0168550 A1 | 7/2010 | Byrd |
| 2010/0168735 A1 | 7/2010 | Deno et al. |
| 2010/0191089 A1 | 7/2010 | Stebler et al. |
| 2010/0256558 A1 | 10/2010 | Olson et al. |
| 2010/0274239 A1 | 10/2010 | Paul |
| 2010/0298823 A1 | 11/2010 | Cao |
| 2011/0015569 A1 | 1/2011 | Kirschenman et al. |
| 2011/0118727 A1 | 5/2011 | Fish et al. |
| 2011/0313311 A1 | 12/2011 | Gaw |
| 2011/0313417 A1 | 12/2011 | De La Rama et al. |
| 2012/0158011 A1 | 6/2012 | Sandhu |

FOREIGN PATENT DOCUMENTS

| | | |
|---|---|---|
| JP | H0851144 | 12/1996 |
| JP | 3585491 | 11/2004 |
| JP | 2005279256 | 10/2005 |
| WO | 98/46149 | 10/1998 |
| WO | 00/78239 | 12/2000 |
| WO | 2007/067628 | 6/2007 |
| WO | 2007/067938 | 6/2007 |
| WO | WO-2007/067941 | 6/2007 |
| WO | WO-2009/065140 | 5/2009 |
| WO | WO-2009/085457 | 7/2009 |
| WO | 2009/20982 | 10/2009 |
| WO | 2011/123669 | 10/2011 |

OTHER PUBLICATIONS

Chakraborty, D.P. , "ROC curves predicted by a model of visual search", *Institute of Physics Publishing, Phys. Med. Biol.* 51 2006 , 3463-3482.

Gao, Xin et al., "Computer-Assisted Quantative Evaluation of Therapeutic Responses for Lymphoma Using Serial PET/CT Imaging", *NIH Public Access, Acad Radiol.* 17(4) Apr. 2010, 1-21.

Himel, Herman D. , "Development of a metric to assess completeness of lesion produced by radiofrequency ablation in the heart", *Dept. of Biomedical Engineering, University of NC, Chapel Hill* 2006 , i-xvii; 1-138.

"International Search Report and Written Opinion of the International Searching Authority", PCT/US2006/061714 Sep. 22, 2008.

Avitall, Boaz et al., "The Effects of Electrode-Tissue Contact on Radiofrequency Lesion Generation", *PACE, vol. 20* Dec. 1997 , 2899-2910.

Cho, Sungbo et al., "Design of electrode array for impedance measurement of lesions in arteries", *Physiol. Meas.* 26 S19-S26 doi:10.1088/0967-3334/26/2/002 2005.

Dumas, John H. et al., "Myocardial electrical impedance as a predictor of the quality of RF-induced linear lesions", *Physiological Measurement, vol. 29* 2008 , Abstract only.

Fenici, R. R. et al., "Biomagnetically localizable multipurpose catheter and method for MCG guided intracardiac electrophysiology, biopsy and ablation of cardiac arrhythmias", *Int'l Journal of Cardiac Imaging* 7, 207-215, 1991.

Gales, Rosemary et al., "Use of bioelectrical impedance analysis to assess body composition of seals", *Marine Mammal Science, vol. 10, Issue 1, Abstract* Aug. 26, 2006.

He, Ding S. et al., "Assessment of Myocardial Lesion Size during In Vitro Radio Frequency Catheter Ablation", *IEEE Transactions on Biomedical Engineering, vol. 50, No. 6* Jun. 2003 , 768-776.

Holmes, Douglas et al., "Tissue Sensing Technology Enhances Lesion Formation During Irrigated Catheter Ablation", *HRS* 2008 , Abstract only.

ISR PCT/US2008/084194, , "ISR mailed Feb. 5, 2009".

Masse, Stephane et al., "A Three-dimensional display for cardiac activation mapping", *Pace, vol. 14* Apr. 1991.

Salazar, Y et al., "Transmural versus nontransmural in situ electrical impedance spectrum for healthy, ischemic, and healed myocardium", *IEEE Xplore, Abstract* 2009.

(56) References Cited

OTHER PUBLICATIONS

Zheng, Xiangsheng et al., "Electrode Impedance: An Indicator of Electrode-Tissue Contact and Lesion Dimensions During Linear Ablation", *Journal of Interventional Cardiac Electrophysiology 4* 2000, 645-654.
Supplementary European Search Report issued in EP Patent Application No. 11842330.0 (Jan. 20, 2014).
Thomas, Stuart P., et al., Comparision of Epicardial and Endocardial Linear Ablation Using Handheld Probes, The Annals of Thoracic Surgery, vol. 75, Issue 2, pp. 543-548, Feb. 2003.
Written Opinion of the International Searching Authority in PCT Application No. PCT/US2006/046565 (May 2, 2007).
International Search Report and Written Opinion in PCT Application No. PCT/US2008/084200 (Jan. 22, 2009)
International Search Report and Written Opinion in PCT Application No. PCT/US2010/034414 (Sep. 1, 2010).
International Search Report and Written Opinion in PCT Application No. PCT/US2006/061716 (Oct. 4, 2007).
International Search Report and Written Opinion in PCT Application No. PCT/US2006/061712 (Oct. 29, 2007).
International Search Report and Written Opinion in PCT Application No. PCT/US2006/061710 (Feb. 15, 2008).
International Search Report and Written Opinion in PCT Application No. PCT/US2006/061711 (Oct. 5, 2007).
International Search Report and Written Opinion in PCT Application No. PCT/US2006/061717 (Oct. 4, 2007).
Supplementary European Search Report in EP Application No. 06839102.8 (Nov. 16, 2009).
Supplementary Partial European Search Report in EP Application No. 06848530.9 (Nov. 17, 2009)
Supplementary European Search Report in EP Application No. 06840133.0 (Nov. 16, 2009).
International Search Report and Written Opinion in PCT Application No. PCT/US2010/034412 (Jun. 29, 2010).
Supplementary European Search Report in EP Application No. 10775417.8 (Oct. 25, 2013).
International Search Report and Written Opinion in PCT Application No. PCT/US2006/061713 (Oct. 3, 2007).
Supplementary European Search Report in EP Application No. 06848530.9 (Nov. 17, 2009).

\* cited by examiner

SYSTEM AND METHOD FOR PRESENTING INFORMATION REPRESENTATIVE OF LESION FORMATION IN TISSUE DURING AN ABLATION PROCEDURE

CROSS REFERENCE TO RELATED APPLICATIONS

This application is a continuation-in-part of U.S. patent application Ser. No. 12/946,941 entitled "System and Method for Assessing the Formation of a Lesion in Tissue" filed Nov. 16, 2010, which is issued as U.S. Pat. No. 8,603,084 and is a continuation-in-part of U.S. patent application Ser. No. 12/622,488 entitled "System and Method for Assessing Lesions in Tissue" filed Nov. 20, 2009, which is issued as U.S. Pat. No. 8,403,925 and which claimed the benefit of U.S. Provisional Application Ser. No. 61/177,876 entitled "System and Method for Assessing Lesions in Tissue" filed May 13, 2009. The entire disclosures of each of the above identified applications are incorporated herein by reference.

BACKGROUND OF THE INVENTION a. Field of the Invention

This disclosure relates to a system and method for presenting information representative of lesion formation in tissue during an ablation procedure. More particularly, this disclosure relates to a system and method for automatically characterizing lesion markers and placing the lesion markers onto an image or model of tissue so as to form a lesion formation map.

b. Background Art

It is known that ablation therapy may be used to treat various conditions afflicting the human anatomy. One such condition that ablation therapy finds particular applicability is in the treatment of atrial arrhythmias, for example. When tissue is ablated, or at least subjected to ablative energy generated by an ablation generator and delivered by an ablation catheter, lesions form in the tissue. More particularly, an electrode or electrodes mounted on or in the ablation catheter are used to create tissue necrosis in cardiac tissue to correct conditions such as atrial arrhythmia (including, but not limited to, ectopic atrial tachycardia, atrial fibrillation, and atrial flutter). Atrial arrhythmias can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radio frequency energy, cryoablation, lasers, chemicals, high-intensity focused ultrasound, etc.) to cardiac tissue to create a lesion in the cardiac tissue. The lesion disrupts undesirable electrical pathways and thereby limits or prevents stray electrical signals that lead to arrhythmias.

One challenge with ablation procedures is in the assessment of the integrity or efficacy of the lesion formed during the ablation procedure. Conventional techniques are both empirical and subjective. More particularly, conventional techniques include the clinician or another user of the system monitoring ablation description characteristics and parameters thereof, interpreting those characteristics/parameters, and manually causing markers to be placed onto an image of the tissue being ablated to represent the monitored characteristics.

Conventional techniques such as these suffer from a number of drawbacks, however. For example, oftentimes ablation description parameters that the clinician monitors are displayed on display monitors of different devices, thereby rendering the monitoring difficult and the interpretation prone to error. Further, many parameters are contaminated with RF, cardiac motion, or respiratory motion artifacts, thereby contaminating the signals, which can lead to errors in both lesion marker location and lesion quality estimation. Additionally, respiratory artifacts and ablation generator (RF) impedance can lead to unreliable measurements, such as, for example, impedance drop measurements. Further, visualization of lesion quality is complicated because clinicians indirectly control lesion marker placement and visualization.

Existing software tools cannot automatically quantify and visualize lesion integrity. In certain existing systems, clinicians manipulate catheters within a sterile field, while a separate operator places lesion markers on a mapping system in a non-sterile field. Therefore, operators, and not catheter manipulating clinicians, are manually placing lesion markers on an image of the tissue being ablated. Once the lesion marker is placed, there is no way to determine whether the operator understood or correctly implemented the clinician's lesion efficacy criteria. Thus, there is no way to determine whether the location and/or the coloration, for example, of the manually-placed lesion markers reflect the clinician's lesion efficacy criteria. As a result, errors in the location of lesion markers can mislead the clinician into erroneously believing that certain areas have been ablated or not ablated. Errors in the coloration and size of the markers can mislead the clinician into erroneously believing that the lesion integrity or efficacy is poor when it is in fact good, or good when it is in fact poor.

Accordingly, the inventors herein have recognized a need for a system and method for characterizing and placing lesion markers on an image of tissue being subjected to an ablation procedure that will minimize and/or eliminate one or more of the deficiencies in conventional systems.

BRIEF SUMMARY OF THE INVENTION

The present invention is directed to a system and method for presenting information representative of lesion formation in tissue during an ablation procedure. The system, in accordance with present teachings, comprises an electronic control unit (ECU). The ECU is configured to acquire a value for at least one of an ablation description parameter and a position signal metric, wherein the value corresponds to a location in the tissue. The ECU is further configured to evaluate the acquired value, and to then assign it a visual indicator of a visualization scheme associated with the ablation description parameter or position signal metric that corresponds to the acquired value. The ECU is still further configured to generate a marker responsive to the evaluation of the acquired value and the assignment of the visual indicator, the marker comprising the visual indicator such that the marker is indicative of the value of the ablation description parameter or position signal metric.

In an exemplary embodiment, the ECU is further configured to determine the location corresponding to the acquired value based on a position of a positioning sensor associated with a medical device, and to associate the acquired value with the location. In an exemplary embodiment, the ECU is further configured to superimpose the generated marker onto a portion of an image or model of the tissue that corresponds to the determined location. Once the marker is superimposed onto the image or model of the tissue, in an exemplary embodiment, the ECU is further configured to control a display device to cause the image or model with the marker superimposed thereon to be displayed thereon.

In another exemplary embodiment, the ECU may be configured to assess the stability of the positioning electrode, and therefore, the medical device with which the positioning electrode is associated. In such an embodiment, the stability assessment may be used for a number of purposes, such as, for example, the characterization of the marker and/or the placement of the marker onto the image or model.

In accordance with another aspect of the invention, a method for presenting information representative of lesion formation in tissue during an ablation procedure is provided. In accordance with the present teachings, the method includes a step of acquiring a value for at least one of an ablation description parameter and a position signal metric, wherein the value corresponds to a location in the tissue. The method further includes the steps of evaluating the acquired value, and assigning a visual indicator of a visualization scheme associated with the ablation description parameter and/or position signal metric that corresponds to the acquired value. The method step further includes the step of generating a marker responsive to the evaluation of the acquired value and assignment of the visual indicator, wherein the marker comprises the visual indicator such that the marker is indicative of the acquired value.

In an exemplary embodiment, the method further includes the steps of determining the location in the tissue corresponding to the acquired value based on a position of a positioning sensor associated with a medical device, and associating the acquired value with the location. In an exemplary embodiment, the method further includes the step of superimposing the generated marker onto a portion of an image or model of the tissue that corresponds to the determined location. Once the marker is superimposed onto the image or model of the tissue, in an exemplary embodiment, the method further includes displaying image or model with the marker superimposed thereon one a display device.

In another exemplary embodiment, the method further includes the step of assessing the stability of the positioning electrode, and therefore, the medical device with which the positioning electrode is associated. In such an embodiment, the stability assessment may be used for a number of purposes, such as, for example, the characterization of the marker and/or the placement of the marker onto the image or model.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
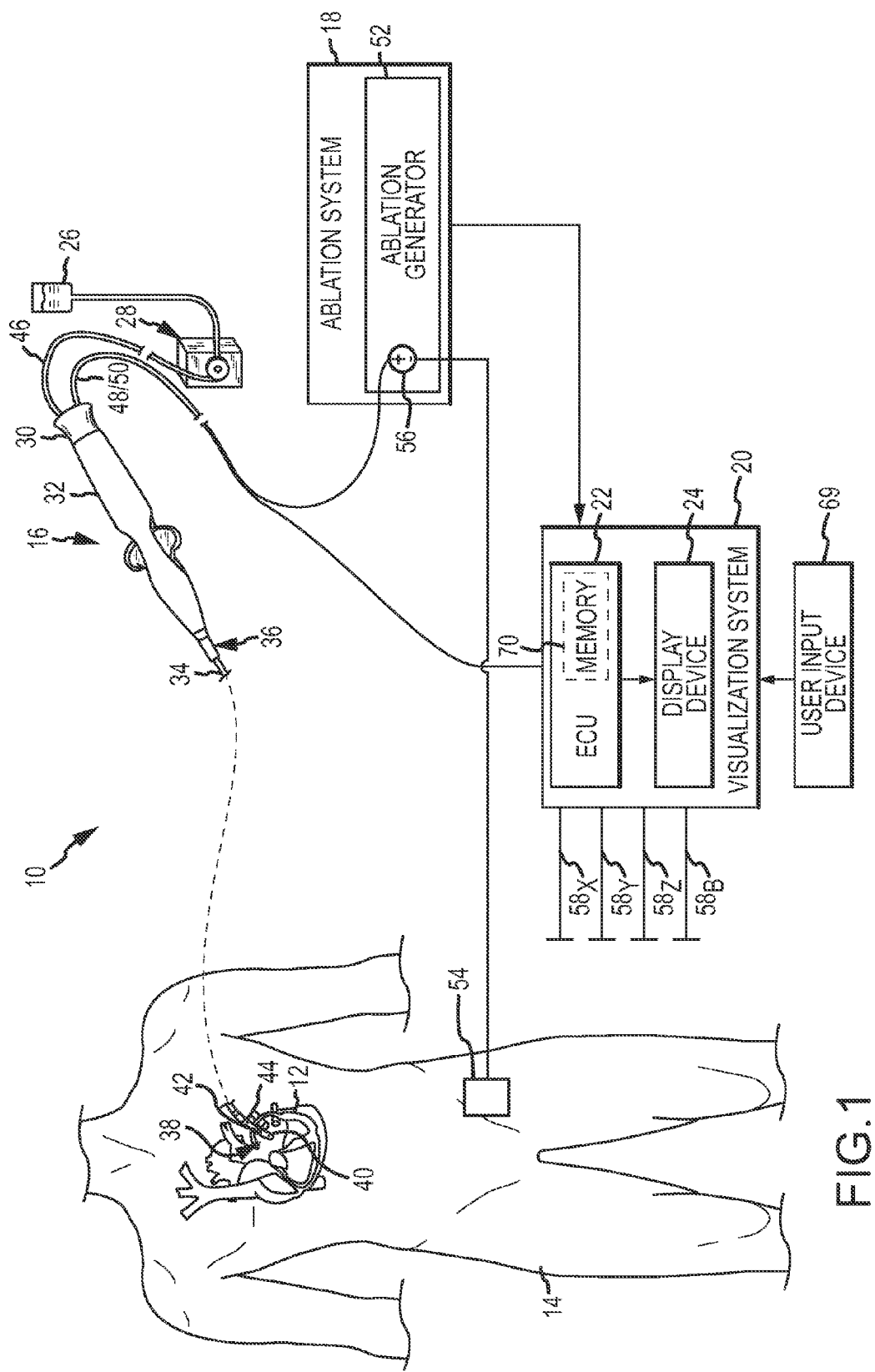
FIG. 1 is diagrammatic view of a system for presenting information relating to lesion formation in tissue in accordance with the present teachings.

Referring now to the drawings wherein like reference numerals are used to identify identical components in the various views, FIG. 1 illustrates one exemplary embodiment of a system 10 for performing one more diagnostic and/or therapeutic functions that includes components for presenting information representative of lesion formation in a tissue 12 of a body 14 during an ablation procedure performed thereon. In an exemplary embodiment, the tissue 12 comprises heart or cardiac tissue within a human body 14. It should be understood, however, that the system 10 may find application in connection with the ablation of a variety of other tissues within human and non-human bodies.

Among other components, the system 10 includes a medical device (such as, for example, a catheter 16) an ablation system 18, and a system 20 for the visualization, navigation, and/or mapping of internal body structures. The system 20 may include, for example and without limitation, an electronic control unit (ECU) 22 and a display device 24. Alternatively, the ECU 22 and/or the display 24 may be separate and distinct from, but electrically connected to and configured for communication with, the system 20.

With continued reference to FIG. 1, the catheter 16 is provided for examination, diagnosis, and/or treatment of internal body tissues such as the tissue 12. In an exemplary embodiment, the catheter 16 comprises an ablation catheter and, more particularly, an irrigated radio-frequency (RF) ablation catheter. It should be understood, however, that catheter 16 is not limited to an irrigated catheter or an RF ablation catheter. Rather, in other embodiments, the catheter 16 may comprise a non-irrigated catheter and/or other types of ablation catheters (e.g., cryoablation, ultrasound, etc.). In the exemplary embodiment wherein the catheter 16 is an irrigated RF catheter, the catheter 16 is connected to a fluid source 26 providing a biocompatible fluid such as saline through a pump 28 (which may comprise, for example, a fixed rate roller pump or variable volume syringe pump with a gravity feed supply from the fluid source 26, as shown) for irrigation.

In an exemplary embodiment, the catheter 16 is electrically connected to the ablation system 18 to allow for the delivery of RF energy. The catheter 16 may include a cable connector or interface 30, a handle 32, a shaft 34 having a proximal end 36 and a distal end 38 (as used herein, "proximal" refers to a direction toward the end of the catheter 16 near the clinician, and "distal" refers to a direction away from the clinician and (generally) inside the body of a patient), and one or more electrodes 40, 42 mounted in or on the shaft 34 of the catheter 16. In an exemplary embodiment, the electrodes 40, 42 are disposed at or near the distal end 38 of the shaft 34, with the electrode 40 comprising an ablation electrode disposed at the extreme distal end 38 of the shaft 34 (i.e., tip electrode 40), and the electrode 42 comprising a positioning electrode used, for example, with the visualization, navigation, and mapping system 20. The catheter 16 may further include other conventional components such as, for example and without limitation, a temperature sensor 44, additional electrodes (e.g., ring electrodes) and corresponding conductors or leads, or additional ablation elements, e.g., a high intensity focused ultrasound ablation element.

The connector 30 provides mechanical, fluid, and electrical connection(s) for cables 46, 48, 50 extending from the pump 28, the ablation system 18, and the visualization, navigation, and/or mapping system 20. The connector 30 is conventional in the art and is disposed at the proximal end 36 of the catheter 16.

The handle 32 provides a location for the clinician to hold the catheter 16 and may further provide means for steering or guiding the shaft 34 within the body 14. For example, the handle 32 may include means to change the length of a guidewire extending through the catheter 16 to the distal end 38 of the shaft 34 to steer the shaft 34. The handle 32 is also conventional in the art and it will be understood that the construction of the handle 32 may vary. In another exemplary embodiment, the catheter 16 may be robotically driven or controlled. Accordingly, rather than a clinician manipulating a handle to steer or guide the catheter 16, and the shaft 34 thereof, in particular, a robot is used to manipulate the catheter 16.

The shaft 34 is an elongate, tubular, flexible member configured for movement within the body 14. The shaft 34 supports, for example and without limitation, the electrodes 40, 42, associated conductors, and possibly additional electronics used for signal processing or conditioning. The shaft 34 may also permit transport, delivery and/or removal of fluids (including irrigation fluids, cryogenic ablation fluids, and bodily fluids), medicines, and/or surgical tools or instruments. The shaft 34 may be made from conventional materials such as polyurethane, and defines one or more lumens configured to house and/or transport electrical conductors, fluids, or surgical tools. The shaft 34 may be introduced into a blood vessel or other structure within the body 14 through a conventional introducer. The shaft 34 may then be steered or guided through the body 14 to a desired location such as the tissue 12 with guidewires or other means known in the art.

With reference to FIG. 1, the ablation system 18 is comprised of, for example, an ablation generator 52 and one or more ablation patch electrodes 54. The ablation generator 52 generates, delivers, and controls RF energy output by the ablation catheter 16 and the tip electrode 40 thereof, in particular. The generator 52 is conventional in the art and may comprise the commercially available unit sold under the model number IBI-1500T RF Cardiac Ablation Generator, available from Irvine Biomedical, Inc. In an exemplary embodiment, the generator 52 includes an RF ablation signal source 56 configured to generate an ablation signal that is output across a pair of source connectors: a positive polarity connector SOURCE (+), which may electrically connected to the tip electrode 40 of the catheter 16; and a negative polarity connector SOURCE(−), which may be electrically connected to one or more of the patch electrodes 54. It should be understood that the term connectors as used herein does not imply a particular type of physical interface mechanism, but is rather broadly contemplated to represent one or more electrical nodes. The source 56 is configured to generate a signal at a predetermined frequency in accordance with one or more user specified parameters (e.g., power, time, etc.) and under the control of various feedback sensing and control circuitry as is known in the art. The source 56 may generate a signal, for example, with a frequency of about 450 kHz or greater. The generator 52 may also monitor various parameters associated with the ablation procedure including, for example, impedance, the temperature at the distal tip of the catheter, applied ablation energy, and the position of the catheter, and provide feedback to the clinician or another component within the system 10 regarding these parameters.

Figure 2:
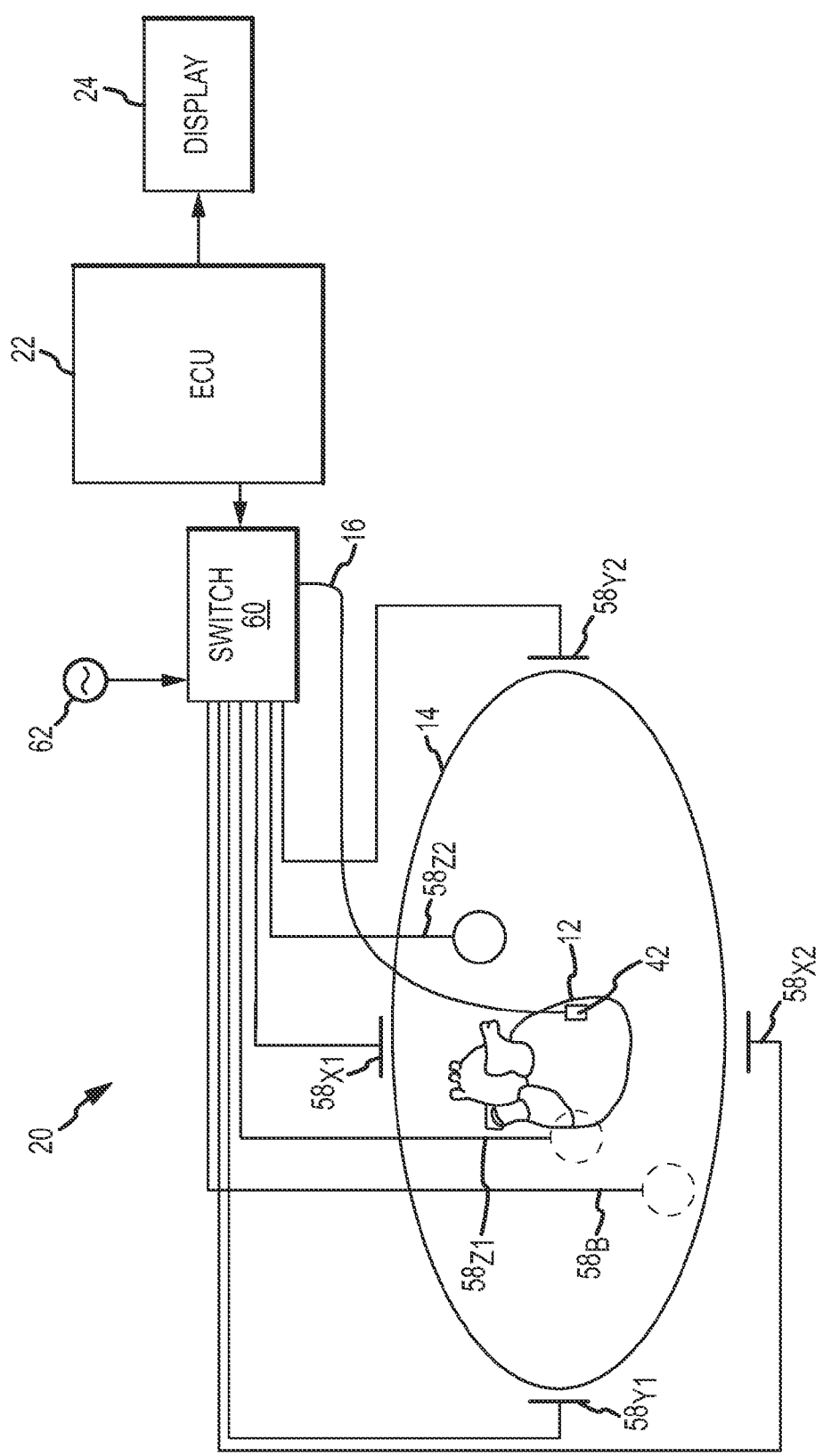
FIG. 2 is a simplified schematic diagram illustrating the visualization, navigation, and mapping system of the system illustrated in FIG. 1.

With reference to FIGS. 1 and 2, the visualization, navigation, and mapping system 20 will be described. The system 20 is provided for visualization, navigation, and/or mapping of internal body structures. The visualization, navigation, and/or mapping system may comprise an electric field-based system, such as, for example, that having the model name EnSite NavX™ and commercially available from St. Jude Medical., Inc. and as generally shown with reference to U.S. Pat. No. 7,263,397 titled "Method and Apparatus for Catheter Navigation and Location and Mapping in the Heart," the entire disclosure of which is incorporated herein by reference. In other exemplary embodiments, however, the visualization, navigation, and/or mapping system may comprise other types of systems, such as, for example and without limitation: a magnetic-field based system such as the Carto™ System available from Biosense Webster, and as generally shown with reference to one or more of U.S. Pat. Nos. 6,498,944 entitled "Intrabody Measurement," 6,788,967 entitled "Medical Diagnosis, Treatment and Imaging Systems," and 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. Nos. 6,233,476 entitled "Medical Positioning System," 7,197,354 entitled "System for Determining the Position and Orientation of a Catheter," and 7,386,339 entitled "Medical Imaging and Navigation System," the entire disclosures of which are incorporated herein by reference; a combination electric field-based and magnetic field-based system such as the Carto 3™ System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference; as well as other impedance-based localization systems, ultrasound-based systems, and commonly available fluoroscopic, computed tomography (CT), and magnetic resonance imaging (MRI)-based systems.

In an exemplary embodiment, the catheter 16 includes a positioning sensor for producing signals indicative of catheter position and/or orientation information, and may include, for example, one or more electrodes (e.g., the electrode 42) in the case of an electric-field based system, or alternatively, one or more magnetic sensors (e.g., coils) configured to detect one or more characteristics of a low-strength magnetic field, for example, in the case of a magnetic field-based system. For purposes of clarity and illustration only, the system 20 will hereinafter be described as comprising an electric field-based system, such as, for example, the EnSite NavX™ identified above. Accordingly, it will be appreciated that while the description below is primarily limited to an embodiment wherein the positioning sensor comprises one or more positioning electrodes (i.e., positioning electrode 42), in other exemplary embodiments, the positioning sensor may comprise one or more magnetic field sensors (e.g., coils). Accordingly, visualization, navigation, and mapping systems 20 that include positioning sensors other than electrodes remain within the spirit and scope of the present disclosure.

With reference to FIGS. 1 and 2, the system 20 may include a plurality of patch electrodes 58, the ECU 22, and the display device 24, among other components. However, as briefly described above, in another exemplary embodiment, the ECU 22 and/or the display device 24 may be separate and distinct components that are electrically connected to, and configured for communication with, the system 20.

With the exception of the patch electrode $58_B$ called a "belly patch," the patch electrodes 58 are provided to generate electrical signals used, for example, in determining the position and orientation of the catheter 16, and in the guidance thereof. In one embodiment, the patch electrodes 58 are placed orthogonally on the surface of the body 14 and are used to create axes-specific electric fields within the body 14. For instance, in one exemplary embodiment, patch electrodes $58_{X1}$, $58_{X2}$ may be placed along a first (x) axis. Patch electrodes $58_{Y1}$, $58_{Y2}$ may be placed along a second (y) axis, and patch electrodes $58_{Z1}$, $58_{Z2}$ may be placed along a third (z) axis. Each of the patch electrodes 58 may be coupled to a multiplex switch 60. In an exemplary embodiment, the ECU 22 is configured through appropriate software to provide control signals to switch 60 to thereby sequentially couple pairs of electrodes 58 to a signal generator 62. Excitation of each pair of electrodes 58 generates an electrical field within body 14 and within an area of interest such as tissue 12. Voltage levels at non-excited electrodes 58, which are referenced to the belly patch $58_B$, are filtered and converted and provided to ECU 22 for use as reference values.

As briefly discussed above, the catheter 16 includes one or more electrodes mounted therein or thereon that are electrically coupled to the ECU 22. In an exemplary embodiment. The positioning electrode 42 (or, in another embodiment, a plurality of positioning electrodes 42) is placed within electrical fields created in the body 14 (e.g., within the heart) by exciting the patch electrodes 58. The positioning electrode 42 experiences voltages that are dependent on the location between the patch electrodes 58 and the position of the positioning electrode 42 relative to tissue 12. Voltage measurement comparisons made between the electrode 42 and the patch electrodes 58 can be used to determine the position of the positioning electrode 42 relative to the tissue 12. Movement of the positioning electrode 42 proximate the tissue 12 (e.g., within a heart chamber) produces information regarding the geometry of the tissue 12. This information may be used by the ECU 22, for example, to generate models and maps of anatomical structures. Information received from the positioning electrode 42 can also be used to display on a display device, such as display device 24, the location and orientation of the positioning electrode 42 and/or the tip of the catheter 16 relative to the tissue 12. Accordingly, among other things, the ECU 22 of the system 20 provides a means for generating display signals used to the control display device 24 and the creation of a graphical user interface (GUI) on the display device 24.

The ECU 22 may also provide a means for determining the geometry of the tissue 12, EP characteristics of the tissue 12, and the position and orientation of the catheter 16. The ECU 22 may further provide a means for controlling various components of system 10 including, but not limited to, the switch 60. It should be noted that while in an exemplary embodiment the ECU 22 is configured to perform some or all of the functionality described above and below, in another exemplary embodiment, the ECU 22 may be separate and distinct from the system 20, and system 20 may have another processor configured to perform some or all of the functionality (e.g., acquiring the position/location of the electrode/catheter, for example). In such an embodiment, the processor of the system 20 would be electrically coupled to, and configured for communication with, the ECU 22. For purposes of clarity and ease of description only, the description below will be limited to an embodiment wherein ECU 22 is part of system 20 and configured to perform the functionality described herein.

The ECU 22 may comprise a programmable microprocessor or microcontroller or may comprise an application specific integrated circuit (ASIC). The ECU 22 may include a central processing unit (CPU) and an input/output (I/O) interface through which the ECU 22 may receive a plurality of input signals including, for example, signals generated by patch electrodes 58, the positioning electrode 42, and the ablation system 18, and generate a plurality of output signals including, for example, those used to control and/or provide data to treatment devices, the display device 24, and the switch 60. The ECU 22 may be configured to perform various functions, such as those described in greater detail below, with appropriate programming instructions or code (i.e., software). Accordingly, the ECU 22 is programmed with one or more computer programs encoded on a computer storage medium for performing the functionality described herein.

In operation, the ECU 22 generates signals to control the switch 60 to thereby selectively energize the patch electrodes 58. The ECU 22 receives position signals (location information) from the catheter 16 (and particularly the positioning electrode 42) reflecting changes in voltage levels on the positioning electrode 42 and from the non-energized patch electrodes 58. The ECU 22 uses the raw location data produced by the patch electrodes 58 and positioning electrode 42 and corrects the data to account for respiration, cardiac activity, and other artifacts using known or hereinafter developed techniques. The ECU 22 may then generate display signals to create an image of the catheter 16 that may be superimposed on an EP map of the tissue 12 generated or acquired by the ECU 22, or another image or model of the tissue 12 generated or acquired by the ECU 22.

Figure 3:
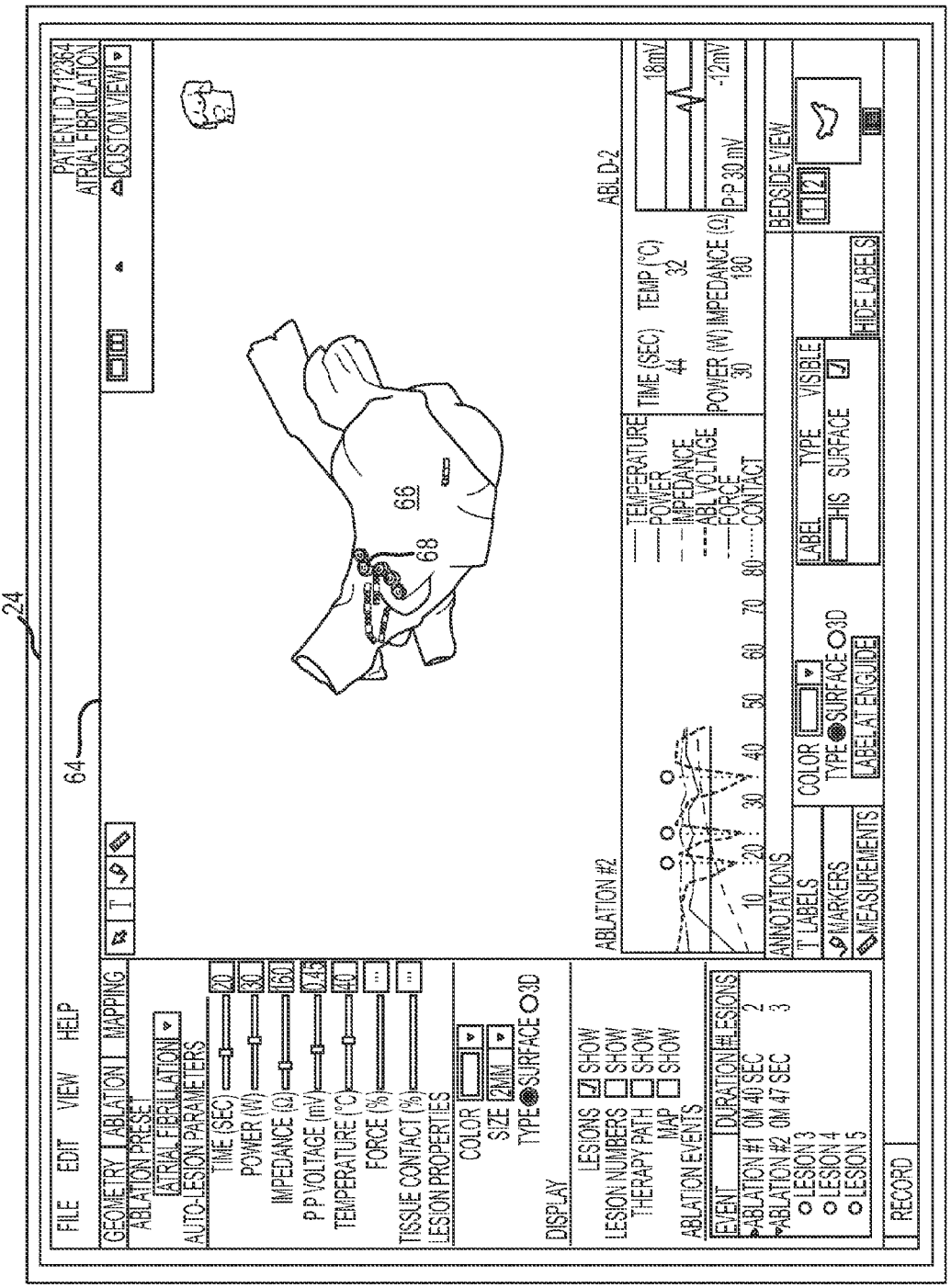
FIGS. 3 and 4 are exemplary embodiments of a display device of the system illustrated in FIG. 1 with a graphical user interface (GUI) displayed thereon.

The display device 24, which, as described above, may be part of the system 20 or a separate and distinct component, is provided to convey information to a clinician to assist in, for example, the formation of lesions in the tissue 12. The display device 24 may comprise a conventional computer monitor or other display device. With reference to FIG. 3, the display device 24 presents a graphical user interface (GUI) 64 to the clinician. The GUI 64 may include a variety of information including, for example and without limitation, an image or model of the geometry of the tissue 12, EP data associated with the tissue 12, electrocardiograms, ablation data associated with the tissue 12 and/or the ablation generator 52, markers corresponding to lesion formation in the tissue 12, electrocardiographic maps, and images of the catheter 16 and/or positioning electrode 42. Some or all of this information may be displayed separately (i.e., on separate screens), or simultaneously on the same screen. As will be described in greater detail below, the GUI 64 may further provide a means by which a clinician may input information or selections relating to various features of the system 10 into the ECU 22.

The image or model of the geometry of the tissue 12 (image/model 66 shown in FIG. 3) may comprise a two-dimensional image of the tissue 12 (e.g., a cross-section of the heart) or a three-dimensional image of the tissue 12. The image or model 66 may be generated by the ECU 22 of the system 20, or alternatively, may be generated by another imaging, modeling, or visualization system (e.g., fluoroscopic, computed tomography (CT), magnetic resonance imaging (MRI), direct visualization, etc. based systems) that are communicated to, and therefore, acquired by, the ECU 22. As briefly mentioned above, the display device 24 may also include an image of the catheter 16 and/or the positioning electrode 42 illustrating their position relative to the tissue 12. The image of the catheter may be part of the image 66 itself or may be superimposed onto the image/model 66.

In an exemplary embodiment, and as will be described in greater detail below, the ECU 22 may be further configured generate the GUI 64 on the display device 24 that, as will be described in greater detail below, enables a clinician to enter various information. The information may relate to, for example, ablation description characteristics or parameters thereof, that the clinician is interested in monitoring, visualization schemes to be associated with one or more ablation description characteristics/parameters, and criteria to be used in evaluating ablation description parameters, such as, for example, the magnitude of evaluation time intervals, the magnitude of various threshold values, stability assessment criteria, and the like.

Figure 4:
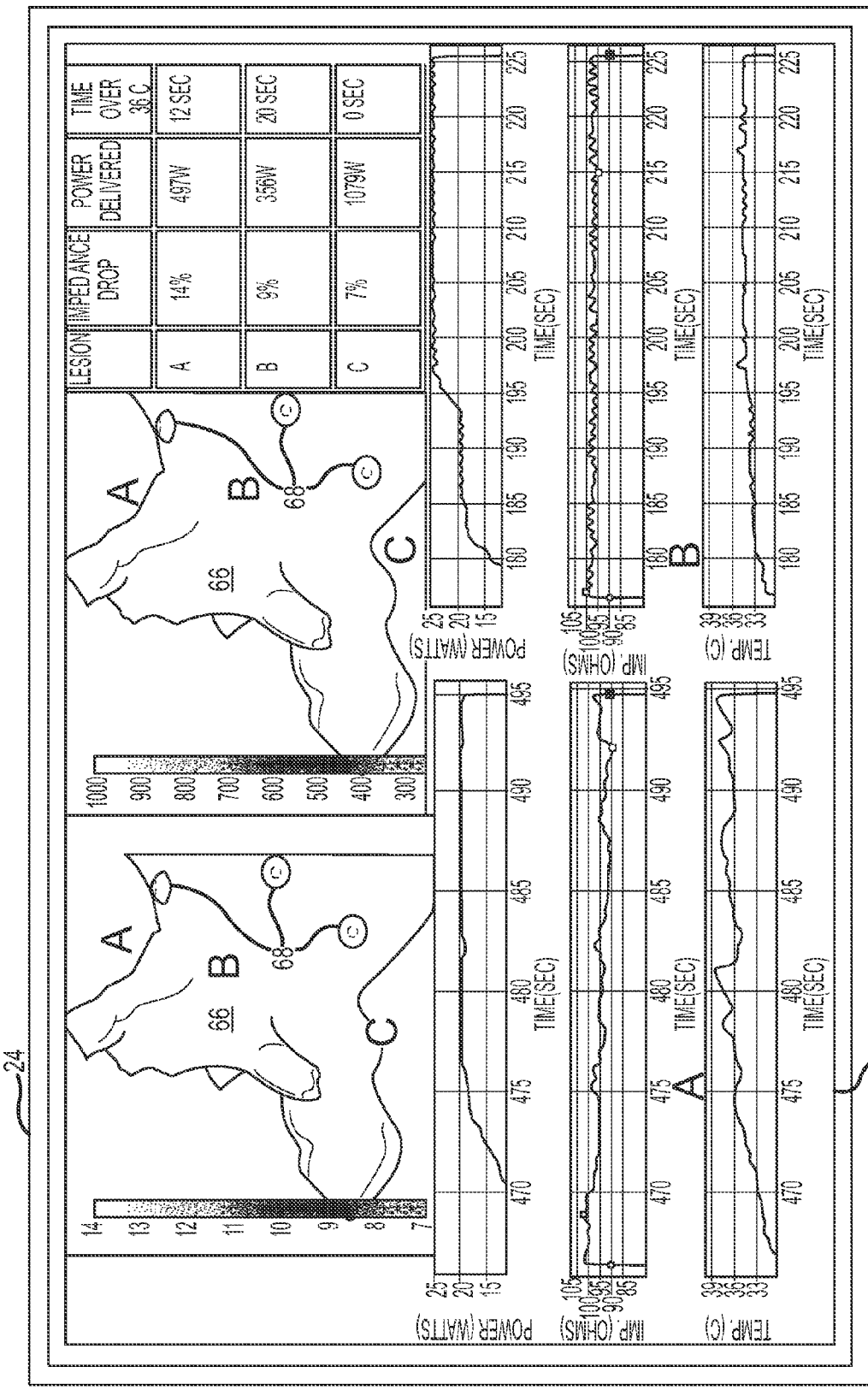

With reference to FIG. 4, in addition to the functionality described above, in an exemplary embodiment, the ECU 22 is further configured to generate one or more lesion markers 68 that may be displayed on a display such as the display device 24, and used to create a lesion formation map. More particularly, and as will be described in greater detail below, in an exemplary embodiment the marker 68 is superimposed onto the image/model 66 of the tissue 12, and then the image/model 66 is displayed on the display device 24 with the marker 68 superimposed thereon. In addition to generating the marker 68, the ECU 22 is further configured to automatically characterize the lesion marker 68 so as to represent various types of information either in response to a command by a user or automatically. Information that may be used to characterize the lesion marker 68 includes, for example and without limitation, one or more ablation description characteristics (or parameters thereof) corresponding to a particular location in the tissue 12, information relating to the position (e.g., the stability) of the positioning electrode 42 (which, in an exemplary embodiment, may alternatively comprise a magnetic sensor (e.g., coil)), and therefore, the catheter 16, and the like. It will be appreciated by those of ordinary skill in the art that while the description above and below is directed primarily to an embodiment wherein the ECU 22 performs this functionality, in another exemplary embodiment system 10 may include another electronic control unit or processor separate and distinct from the ECU 22 and system 20 that is configured to perform the same functionality in the same manner as that described above and below with respect to the ECU 22. Accordingly, the description wherein the ECU 22 alone is configured to perform this functionality is provided for exemplary purposes only and is not meant to be limiting in nature.

Figure 5:
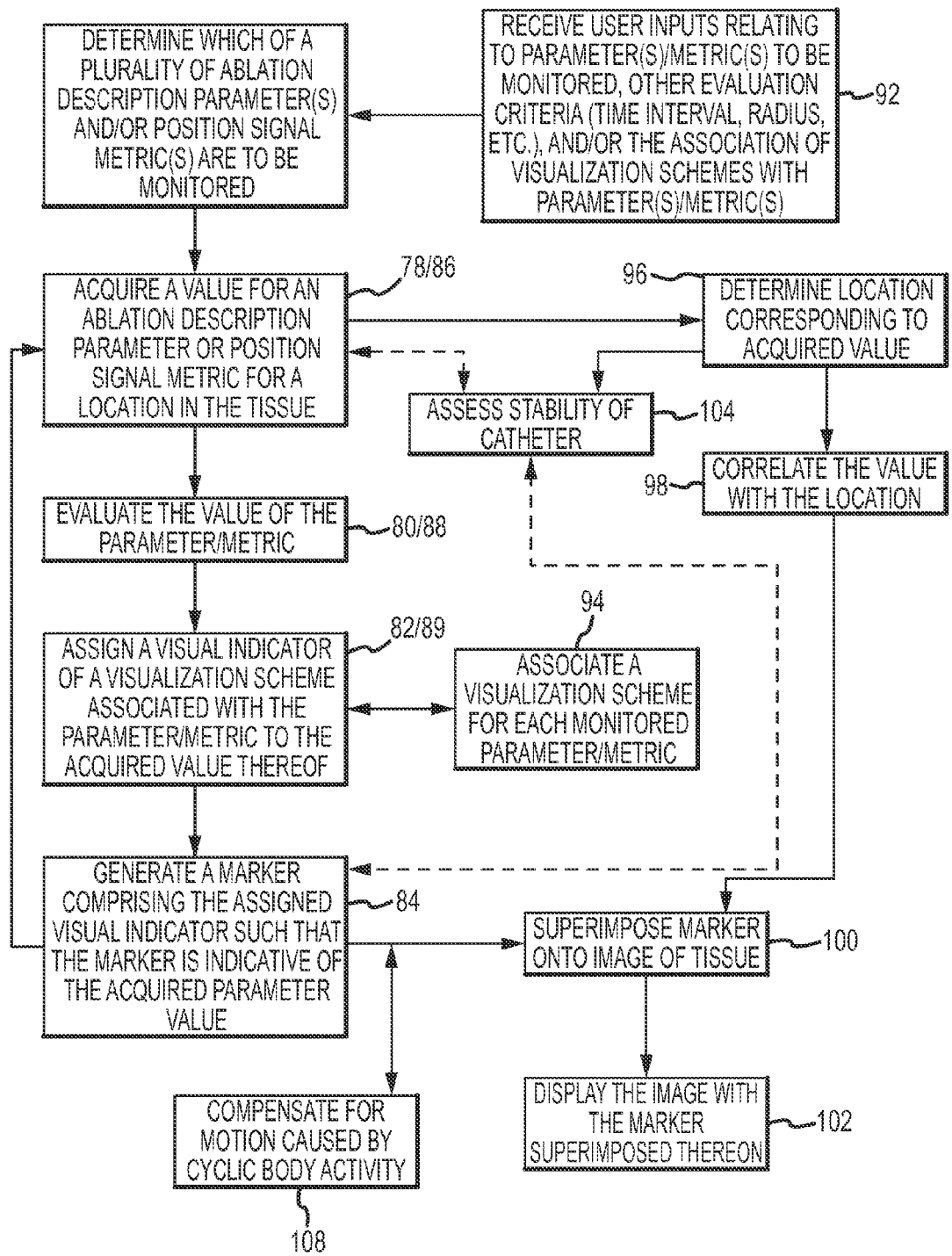
FIG. 5 is flow chart illustrative of an exemplary embodiment of a method for presenting information relating to lesion formation in tissue in accordance with the present teachings.

With reference to FIG. 5, in an exemplary embodiment, the ECU 22 is configured to acquire a value for at least one ablation description parameter corresponding to a particular location in the tissue 12. The ablation description parameter is a parameter of at least one ablation description characteristic that a clinician may be interested in monitoring during the performance of an ablation procedure in order to allow real-time monitoring of lesion formation in tissue. As will be described in greater detail below, the particular ablation description characteristic and corresponding parameter may be selected by the clinician from a set of characteristics/parameters using, for example, the GUI 64, or a user input device 69 associated therewith, or the ECU 22 may be preprogrammed with the parameter(s) to be monitored. Any number of ablation description characteristics and parameters thereof may be monitored and used as described herein.

For example, characteristics monitored by the ablation system 18 may be used. These characteristics include power delivered to the tissue 12 (e.g., the total or average power over a defined time interval, the instantaneous power, etc.), the temperature at the ablation electrode 40 (e.g., the instantaneous temperature, the average temperature over a defined time interval, etc.), the impedance of the tissue 12 (e.g., the instantaneous impedance, the average impedance over a defined time interval, etc.), the detected voltage amplitude, and/or combinations thereof. The means by which these characteristics may be monitored by the ablation system 18 are well known in the art, and therefore, will not be discussed in greater detail.

In addition, or alternatively, characteristics monitored by the visualization, navigation, and/or mapping system 20, or another system in the system 10, may be used. For example, electrograms, and the changes thereto, such as, for example, amplitude reduction during lesion formation, changes in shape/spectrum as a result of the application of ablative energy, and the like may be used. Means by which electrograms may be monitored by either the system 20 or another system are well known in the art, and therefore, will not be discussed in greater detail.

An additional ablation description characteristic may include the degree of contact between the catheter 16, and an electrode or sensing element (e.g., the electrodes 40, 42 or another electrode associated with the catheter 16) thereof, in particular, and the tissue 12. More particularly, in an exemplary embodiment, the system 10 is configured to acquire values for one or more components of the complex impedance between an electrode and the tissue 12, and to calculate an electrical coupling index (ECI) responsive thereto. The raw ECI may then displayed on a display and can be used/interpreted by a clinician to assess the degree of contact between the catheter and the tissue. The raw ECI may also be used by the ECU 22 to assess the degree of contact between the electrode and the tissue 12. Alternatively, it is contemplated that the calculated ECI may be compared to one or more predetermined threshold values, or looked up in a look-up table stored in a storage medium or memory 70 (best shown in FIG. 1) that is part of or accessible by the ECU 22. A determination with respect to the degree of contact may then be made by the ECU 22 based on predetermined criteria, and an indication representative of the determination may be provided to the clinician via a display device (e.g., display 24).

A detailed description of an exemplary approach of calculating the ECI and assessing the degree of contact is set forth in U.S. Patent Publication No. 2009/0163904, filed May 30, 2008 and entitled "System and Method for Assessing Coupling Between an Electrode and Tissue," the entire disclosure of which is incorporated herein by reference. To summarize, the system 10 may include, for example, a tissue sensing circuit, such as a tissue sensing signal source, that is configured to generate an excitation signal used in impedance measurements, and means, such as a complex impedance sensor, for resolving detected impedance into its component parts. The signal source is configured to generate an one or more excitation signals across connectors SOURCE (+) and SOURCE (−). In an exemplary embodiment, the excitation signal is configured to develop a corresponding AC response voltage or current signal, depending on whether the excitation signal is a voltage or current signal, that is dependent on the complex impedance of the tissue 16, which is sensed by the complex impedance sensor. The sensor then resolves the impedance into its component parts, namely, resistance (R) and reactance (X) or the impedance magnitude (|Z|) and phase angle ($\angle Z$ or $\phi$)). One or more components of the complex impedance may then be used by the ECU 22 to calculate the ECI. For example, in one embodiment provided for exemplary purposes only, the ECI is calculated using the equation (1):

$$ECI = a*R\text{mean} + b*X\text{mean} + c \quad (1)$$

wherein Rmean is the mean value of a plurality of resistance values, Xmean is the mean value of a plurality of reactance values, and a, b, and c are coefficients dependent upon, among other things, the specific catheter used, the patient, the equipment, the desired level of predictability, the species being treated, and disease states. More specifically, for one particular 4 mm irrigated tip catheter, the ECI is calculated using the equation (2)

$$ECI = R\text{mean} - 5.1*X\text{mean} \quad (2)$$

Another exemplary ablation description characteristic may be the proximity of the catheter 16, and an electrode thereof, in particular, to the tissue 12. The proximity may be determined using ECI calculated as described above.

A detailed description of an exemplary approach or technique for determining proximity based on ECI is set forth in U.S. Patent Publication No. 2009/0275827 entitled "System and Method for Assessing Proximity of an Electrode to Tissue in a Body," the entire disclosure of which is incorporated herein by reference. To summarize, in one exemplary embodiment, the ECU 22 calculates the ECI and then uses the calculated ECI to assess proximity. More particularly, the calculated ECI may be compared to a predefined ECI range having a first threshold that corresponds to the ECI value at which it is expected that the electrode is in contact with the tissue, and a second threshold that corresponds to the ECI value at which it is expected that the electrode is a predetermined distance away from the tissue (i.e., the electrode is in "close proximity to the tissue). Depending on where the calculated ECI falls with respect to the ECI range, the ECU 22 is configured to determine whether the electrode is in contact with the tissue (when the ECI meets or is below the first threshold), is in close proximity to the tissue (when the ECI falls within the ECI range), or is not in proximity to the tissue (when the ECI exceeds the second threshold). Accordingly, in this embodiment, the raw calculated ECI, or the calculated ECI having an offset applied thereto, is used to determine the proximity of the electrode to the tissue.

In another exemplary embodiment, rather than comparing the finite ECI to a predefined ECI range, the rate of change of the ECI may be evaluated and used to assess proximity. It has been found that when an electrode is within a predetermined distance from the tissue, the rate of change in the ECI is greater than when the electrode is either in contact with, or far away from tissue. Accordingly, when the rate of change of the ECI over a given period of time is within a certain range or equals a particular rate, the ECU 22 can determine the proximity of the electrode to tissue. More specifically, in one exemplary embodiment, the ECU 22 calculates the ECI. The ECU 22 then retrieves one or more previously calculated ECIs (stored, for example, in the memory 70) and calculates the rate of change/slope between the most recent ECI and the one or more previously calculated ECIs. The ECU 22 then determines whether the electrode can be said to be in close proximity to the tissue based on the calculated rate of change/ slope. Accordingly, in this embodiment, the change in the ECI, rather than the raw or adjusted calculated ECI, is used to determine the proximity of the electrode to the tissue.

In yet another exemplary embodiment, if the general position and speed of the tip of the catheter 16 and the electrode mounted thereon are known, the position and speed of the electrode can be combined with ECI to define an ECI rate (ECIR) that is indicative of the rate of change in the ECI as the electrode approaches the tissue. More particularly, the ECU 22 calculates changes in ECI and the distance or position of the electrode over a given time interval. The change in the ECI is then divided by the change in the distance/position to calculate the ECIR. The ECU 22 may then use the calculated ECIR to assess proximity. For example, the ECU 22 may compare the calculated ECIR with a predefined ECIR range in the same manner described above with respect to the comparison of a calculated ECI and an ECI range. Depending on where the ECIR falls with respect to the ECIR range, the ECU 22 may determine whether the electrode is in contact with, in close proximity to, or far away from the tissue. In another exemplary embodiment, the rate of change of the ECIR may be used to assess proximity. Accordingly, in this embodiment, the rate of change in the ECI, rather than the raw or adjusted calculated ECI, or the change in ECI, is used to determine the proximity of the electrode to the tissue.

Yet another ablation description characteristic may be an index representative of the formation of a lesion in the tissue 12. More particularly, an index, such as, for example, ECI or an ablation lesion index (ALI) may be used to assess the formation of lesions in tissue, and more specifically, whether a particular area of tissue at a particular location has been changed (e.g., ablated).

A detailed description of an exemplary approach or technique for assessing the formation of lesions in tissue using ECI and other indices is set forth in U.S. Patent Publication No. 2010/0069921 entitled "System and Method for Assessing Lesions in Tissue," the entire disclosure of which is incorporated herein by reference. To summarize, in an exemplary embodiment, ECI is used to assess lesion formation. It has been found that ECI of changed (e.g., ablated) tissue is lower than that of otherwise similar unchanged or not sufficiently changed (e.g., unablated or not fully ablated) tissue. Accordingly, the catheter 16, and one or more electrodes thereof, such as, for example electrodes 40, 42, or another electrode, in particular, contacts the tissue 12 and is moved along or across the surface of the tissue 12. As the electrode moves, ECI calculations are made by, for example, the ECU 22 in the same manner described above. The ECU 22 is configured to evaluate or process the calculations to enable a determination to be made as to whether the areas or portions of the tissue in contact with the electrode have been changed to such an extent to cause a change in the ECI.

In one exemplary embodiment, the ECU 22 is configured to compare the calculated ECI for a particular location in the tissue 12 to a preset value to determine if a lesion has been formed. In another exemplary embodiment, the ECU 22 may be configured to look up the calculated ECI value in a look-up table that is stored in ECU 22 or accessible thereby (e.g., the memory 70) to determine whether the calculated ECI represents changed or unchanged tissue. In still another exemplary embodiment, the calculated ECI value may be compared to a predefined range to make the determination. In yet still another embodiment, the calculated ECI may be compared to a prior calculated ECI corresponding to the same location in the tissue to determine whether the tissue has changed.

Alternatively, as described above with respect to assessing proximity, changes in ECI over time and/or distance may be evaluated and used to assess lesion formation. More particularly, the ECU 22 may be configured to calculate the change in ECI or either time or distance. For instance, the ECU 22 may be configured to compare a previously calculated ECI with the most recent ECI calculation to determine if there has been a change in ECI, and if so, the degree and/or nature of the change. In an exemplary embodiment, no change is indicative of the electrode remaining in contact with the same type of tissue (i.e., the electrode has not moved from unchanged or not sufficiently changed tissue to changed tissue, or vice versa). If, however, there has been a change, a "positive" change value is indicative of the electrode moving from unchanged to changed tissue. Conversely, a "negative" change value is indicative of the electrode moving from changed to unchanged tissue. The magnitude or degree of the change value may also be considered such that, for example, the amount of change must meet a predetermined threshold to be considered a change in contact between changed and unchanged tissue or vice versa.

In another exemplary embodiment, a rate of change in ECI and/or the ECIR during an ablation procedure may also be considered in assessing lesion formation in the same manner described above with respect to proximity assessment. Accordingly, the ECI, or derivatives thereof, may be used in any number of ways to assess lesion formation in tissue.

Rather than using ECI to assess lesion formation, other indices that take into account the complex impedance, or components thereof, as well as other variables, such as, for example, temperature, pressure, contact force, saline flow rate through the catheter, blood flow rate across the catheter, trabeculation, and/or other parameters that may have an impact on ECI even though contact has not changed may be evaluated. One such index is an ablation lesion index (ALI).

In an exemplary embodiment, an ALI derived from ECI is defined and calculated. ALI takes into account ECI as well as confounding factors, such as, for example, those enumerated above. Accordingly, the catheter 16 may further include additional sensors/electrodes, such as, for example, the temperature sensor 44, force sensors, etc. that are configured to obtain measurements for the corresponding factors. In one exemplary embodiment, the ALI is calculated taking into account temperature and force, in addition to ECI. Accordingly, the ECU 22 is configured to receive inputs comprising components of complex impedance, contact force, and temperature, and to calculate the ALI using, for example, equation (3):

$$ALI = a_1*ECI + a_2*T + a_3*F \quad (3)$$

wherein the ECI, T, and F are calculated or measured values of each of the ECI, temperature (T), and contact force (F) at a particular position or location of the tissue at a particular time, and the coefficients $a_1$, $a_2$, $a_3$ are predetermined values intended to account for the dependent relationship between each of the respective variables and other measurements/calculations.

Regardless of how the ALI is calculated, the ECU 22 is configured to use the calculated ALI to assess whether tissue has been changed, as well as the quality or extent of the change. In an exemplary embodiment, the ALI is compared to a predetermined threshold representative of the minimum ALI level for which contact between the electrode and unchanged or insufficiently changed tissue is attained. If the calculated ALI exceeds the threshold, a determination can be made that the tissue has been changed; otherwise, the tissue is unchanged or at least not sufficiently changed. In another exemplary embodiment, rather than comparing the ALI to a single threshold, the ALI is compared a first and a second threshold, wherein the first threshold corresponds to an ALI value indicative of the tissue being unchanged/insufficiently changed, and the second threshold corresponds to an ALI value indicative of the tissue being changed/sufficiently changed. Depending on where the calculated ALI falls with respect to the thresholds, a determination can be made as to whether the tissue has been changed, and if so, the extent or nature of the change.

As with the ECI described above, in other exemplary embodiments the change in the ALI, the rate of change in the ALI, and the change in the rate of change in the ALI, among others, can be used in the lesion formation assessment in the same manner described above with respect to ECI and assessing proximity. Accordingly, the ALI, or derivatives thereof, may be used in any number of ways to assess lesion formation in tissue.

Yet still another ablation characteristic may include the likelihood of a barotrauma occurring in the tissue 12 during lesion formation process of the ablation procedure. More particularly, the ECU 22 may be configured to determine, based on any number of factors, the likelihood of barotrauma occurring in the tissue 12 during an ablation procedure being performed thereon.

A detailed description of exemplary approaches or techniques for determining the likelihood of barotrauma occurrence in tissue during the application of ablative energy is set forth in U.S. Provisional Patent Application Ser. No. 61/285,756, filed Dec. 11, 2009 and entitled "System and Method for Determining the Likelihood of Endocardial Barotrauma in Tissue During Ablation," and U.S. patent application Ser. No. 12/964,956, filed Dec. 10, 2010, and entitled "Systems and Method for Determining the Likelihood of Endocardial Barotrauma in Tissue During Ablation" the entire disclosures of which are incorporated herein by reference. To summarize, in an exemplary embodiment, the ECU 22 is configured to calculate an index that is indicative of a likelihood of barotrauma or "steam pop" occurring in the tissue.

In an exemplary embodiment, the index is responsive to values for one or more components of the complex impedance between the electrode and the tissue. In an exemplary embodiment, the index is further responsive to value(s) of the power or energy applied to the tissue through the electrode. More particularly, in one embodiment, the index is calculated using equation (4):

$$\text{Index} = a + b_1 * \frac{dR}{dt} + b_2 * I + b_3 * dR + b_4 * dX \quad (4)$$

wherein: dR and dX are the changes in the resistance and reactance, respectively, from the start of the lesion formation process to a subsequent point in time in the formation process of the same lesion; dt is the change in time from the start of the lesion formation process to the subsequent point in time (i.e., the time for which the index is calculated); and I is an electrical current value calculated by taking the square root of the quotient of the division of the mean value of the RF power applied to the tissue from the start of the lesion formation process to the subsequent point in time for which the index is calculated, by the value of the resistance between the electrode and the tissue at a point in time just prior to the start or onset of the lesion formation process. Further, constant $\alpha$ and the coefficients $b_1$-$b_4$ are predetermined values that are intended to account for various factors associated with, for example, the equipment used in the ablation procedure (e.g., the type of catheter and/or ablation generator, irrigation flow rate, etc.).

More specifically, in one embodiment provided for exemplary purposes only where the catheter is a 4 mm open irrigated RF ablation catheter available from St. Jude Medical, Inc. under the name "Cool Path" and an IBI-1500T011 RF Cardiac Ablation Generator available from Irvine Biomedical, Inc., the best prediction of endocardial barotrauma for a system employing the aforementioned components was determined to be equation (5):

$$\text{Index} = -16.4174 + 2.20852 * \frac{dR}{dt} + 0.0191087 * I + 0.0822815 * dR + 0.622496 * dX \quad (5)$$

This equation is provided for exemplary purposes only and is not meant to be limited in nature. Accordingly, the ECU 22 is configured to acquire values for the components of the complex impedance (e.g., from a complex impedance sensor, for example), and, in an exemplary embodiment, the power applied to the tissue during the lesion formation process (e.g., from the ablation generator, for example), to perform the calculations required to get the terms of the equation, and to then calculate the index responsive to those values.

In an exemplary embodiment, once the index is calculated, the ECU 22 is configured to compare the calculated index to a predetermined threshold value stored on or accessible by ECU 22 (e.g., stored in the memory 70). The threshold may correspond to the minimum index value at which barotrauma occurs or, alternatively, may be the maximum index value at which barotrauma will not occur. Based on the comparison, the ECU 22 is may determine whether or not barotrauma is likely to occur. In another exemplary embodiment, the ECU 22 may be configured to evaluate the index other than by comparing it to a threshold value. For example, ECU 22 may look up the calculated index in a look-up table stored on or accessible by the ECU 22 to determine the likelihood of barotrauma occurring in the tissue. Accordingly, the ECU 22 is configured to calculate an index that may be used to assess or determine the likelihood of barotrauma occurring in the tissue being evaluated.

Additional ablation description characteristics may include a predicted depth of a lesion in the tissue 12, the likelihood of a lesion achieving or reaching a predetermined depth in the tissue 12, and a predicted temperature of the tissue 12. More particularly, the ECU 22 may be configured to (i) assess the depth of a lesion being formed in the tissue 12 by either predicting the depth of the lesion or determining the likelihood the lesion has reached a predetermined depth, or (ii) predict the temperature of the tissue 12 at a predetermined depth below the tissue surface.

A detailed description of an exemplary approach or technique for assessing the depth and/or temperature of the tissue is set forth in U.S. patent application Ser. No. 12/946,941 filed Nov. 16, 2010 and entitled "System and Method for Assessing the Formation of a Lesion in Tissue," the entire disclosure of which is incorporated herein by reference. To summarize, however, in an exemplary embodiment, the ECU 22 is configured to calculate a value responsive to magnitudes of one or more components of the complex impedance between an electrode and the tissue 12, and the magnitude of the power or energy applied to the tissue 12 through the electrode, with the calculated value being indicative of one of, for example, a predicted depth of a lesion formed in the tissue, a likelihood that the lesion has reached a predetermined depth, and a temperature of the tissue in which the lesion is being formed. Each one of these characteristics will be briefly described below.

With respect to predicting the depth of a lesion, a lesion depth prediction algorithm is used to calculate a depth of the lesion. In an exemplary embodiment, the calculated depth is responsive to values for one or more components of the complex impedance, namely, the resistance and phase angle components, the average power applied to the tissue, and the duration of the lesion formation process. More particularly, in one embodiment, the depth is calculated using equation (6):

$$\text{Pred. Depth} = a + b_1(\ln \text{Avg.}P) + b_2(dt) + b_3(\text{pre-ablation } \phi) + b_4(dR) + b_5(d\phi) \quad (6)$$

wherein: Avg.P is the average power applied to the tissue during the lesion formation process, dt is the change in time from the start of the lesion formation process to the subsequent point in time (i.e., the time for which the depth is calculated); dR and dφ are the change in resistance and phase angle from the start of the lesion formation process to the subsequent point in time; and pre-ablation φ is the phase angle just prior to the onset of the lesion formation process. Further, constant α and the coefficients $b_1$-$b_5$ are predetermined values that are intended to account for various factors associated with, for example, the equipment used in the ablation procedure (e.g., the type of catheter and/or ablation generator, irrigation flow rate, etc.).

More specifically, in one embodiment provided for exemplary purposes only where the catheter used is an RF ablation catheter available from St. Jude Medical, Inc. under the name "GEN3" and the ablation generator is a 485 kHz generator, the best prediction of lesion depth for a system employing the aforementioned components was determined to be equation (7):

$$\text{Pred. Depth} = -12.1 + 1.92(\ln \text{Avg.}P) + 1.94(dt) - 0.454(\text{pre-ablation } \phi) + 0.0450(dR) + 0.384(d\phi) \quad (7)$$

This equation is provided for exemplary purposes only and is not meant to be limited in nature. Accordingly, the ECU 22 is configured to acquire values for the components of the complex impedance (e.g., from a complex impedance sensor, for example), and the power applied to the tissue during the lesion formation process (e.g., from the ablation generator, for example), to perform the calculations required to get the terms of the equation (or, in the case of the average power, for example, to acquire the results of the calculations from another component in the system 10, such as the ablation generator), and to then calculate the predicted depth using those terms and values. It will be appreciated that in addition to calculating the predicted depth, the ECU 22 may be further configured to determine or acquire the location of the tissue to which the calculated depth corresponds using, for example, the techniques described above in the description of the visualization, navigation, and mapping system 20.

With respect to determining the likelihood that the lesion has reached a predetermined depth, the ECU 22 is configured to calculate an index indicative of the likelihood that the lesion has reached a predetermined depth. In an exemplary embodiment, the index corresponding to a depth of, for example 2 mm, is responsive to values for one or more components of the complex impedance, namely, the resistance and reactance components, the power applied to the tissue during the lesion formation process, and the duration of the lesion formation process. More particularly, for the particular equipment used and for a depth of 2 mm, the index is responsive to the ECI of the tissue, which is based on the resistance and reactance, the duration of the lesion formation process, and the average power applied to the tissue during the lesion formation process. Accordingly, in this embodiment, the index is calculated using equation (8):

$$\text{Index}(2\text{ mm}) = a + b_1 \text{Avg.}P + b_2(\ln dt) + b_3(dECI) \quad (8)$$

wherein Avg.P is the average power applied to the tissue during the lesion formation process, dt is the change in time from the start of the lesion formation process to the subsequent point in time (i.e., the time for which the depth is calculated); and dECI is the change in ECI from the start of the lesion formation process to the subsequent point in time. Further, constant $\alpha$ and the coefficients $b_1$-$b_5$ are predetermined values that are intended to account for various factors associated with, for example, the equipment used in the ablation procedure (e.g., the type of catheter and/or ablation generator, irrigation flow rate, etc.).

More specifically, in one embodiment provided for exemplary purposes only where the catheter used is an RF ablation catheter available from St. Jude Medical, Inc. under the name "Cool Path" and the ablation generator is a 485 kHz generator, the best algorithm for determining the likelihood of a lesion reaching a target depth of 2 mm for a system employing the aforementioned components was determined to be equation (9):

$$\text{Index}(2\text{ mm}) = -12.2 + 0.23\text{Avg.}P + 1.94(\ln dt) + 0.11(dECI) \quad (9)$$

This equation is provided for exemplary purposes only and is not meant to be limited in nature. Accordingly, the ECU 22 is configured to acquire values for the components of the complex impedance (e.g., from a complex impedance sensor, for example), and the power applied to the tissue during the lesion formation process (e.g., from the ablation generator, for example), to perform the calculations required to get the terms of the equation (or, in the case of the average power, for example, to acquire the results of the calculations from another component in the system 10, such as the ablation generator), and to then calculate the index using those terms and values. It will be appreciated that in addition to calculating the predicted depth, the ECU 22 may be further configured to determine or acquire the location of the tissue to which the calculated depth corresponds using, for example, the techniques described above in the description of the visualization, navigation, and mapping system 20.

Once calculated, the ECU 22 is configured to compare the calculated index to a predetermined threshold, which may be stored in the ECU 22 or accessible thereby (e.g., in the memory 70, for example), to determine whether it is likely the lesion has attained the predetermined depth (i.e., if the index exceeds the threshold, the lesion has attained the predetermined depth, while if the index is below the index, the lesion has not attained the predetermined depth). In another exemplary embodiment, algorithms for more than one depth may be used in concert to better assess the depth of the lesion.

With respect to predicting the temperature of the tissue, the ECU 22 is configured to calculate a predicted temperature of the tissue a predetermined depth below the tissue surface. In an exemplary embodiment, the calculated temperature is responsive to values for one or more components of the complex impedance, the power applied to the tissue, the duration of the lesion formation process, and the temperature of the tip of the catheter. More particularly, in one embodiment, the temperature of the tissue a depth of 3 mm below the surface of the tissue is calculated using equation (10):

$$\text{Temp.} = a + b_1 X + b_2 R + b_3 P + b_4 T + b_5 Z + b_6(P^*(dt)) + b_7(d\phi) + b_8(\ln dt) + b_9(\ln P) \quad (10)$$

wherein: X is the reactance between the electrode and the tissue, R is the resistance between the electrode and the tissue, P is the instantaneous power applied to the tissue at the point in time at which the calculation is made, dt is the duration of the lesion formation process, d$\phi$ is the pre-ablation change in the phase angle between when the electrode contacts the tissue and prior to the electrode contacting the tissue. Further, constant $\alpha$ and the coefficients $b_1$-$b_9$ are predetermined values that are intended to account for various factors associated with, for example, the equipment used in the ablation procedure (e.g., the type of catheter and/or ablation generator, irrigation flow rate, etc.).

More specifically, in one embodiment provided for exemplary purposes only where the catheter used is an RF ablation catheter available from St. Jude Medical, Inc. under the name "CoolPath" and the ablation generator is a 485 kHz generator, the best prediction of temperature of the tissue 3 mm below the endocardial surface of the tissue for a system employing the aforementioned components was determined to be equation (11):

$$\text{Temp.} = -577 - 2.44X - -1.37R - 6.88P + 3.05T + 3.29Z + 0.0377(P^*(dt)) + 21.1(d\phi) - 14.1(\ln dt) + 167(\ln P) \quad (11)$$

This equation is provided for exemplary purposes only and is not meant to be limited in nature. Accordingly, the ECU 22 is configured to acquire values for the components of the complex impedance (e.g., from a complex impedance sensor, for example), the power applied to the tissue during the lesion formation process (e.g., from the ablation generator, for example), and the temperature at the tip of the catheter (e.g., from a temperature sensor (e.g., the temperature sensor 44) comprising, for example, a thermocouple, that is electrically connected to and configured for communication with either the ablation generator 52 or the ECU 22) to perform the calculations required to get the terms of the equation. With respect to the change in pre-ablation phase angle, the ECU 22 is further configured to acquire the phase angle prior to the electrode contacting the tissue, as well as after the electrode contacts the tissue. Accordingly, the ECU 22, or another component of the system 10 is further configured to sense or determine when contact is made using any number of different contact sensing techniques (e.g., force sensors, ECI, electrically-measured parameters, visualization techniques, etc.), and to then acquire the phase angle between the electrode and the tissue. Once values for these parameters are acquired, the ECU 22 is further configured to then calculate the predicted temperature using those terms and values. It will be appreciated that in addition to calculating the predicted temperature, the ECU 22 may be further configured to determine or acquire the location of the tissue to which the calculated depth corresponds using, for example, the techniques described above in the description of the visualization, navigation, and mapping system 20.

In an exemplary embodiment, the ablation description characteristics may further include the magnitude of power that is dissipated close to the ablation electrode 40, and the impedance drop between the tissue 12 and an electrode of the catheter 16. These characteristics may be determined using techniques well known in the art, and therefore, a detailed description will not be provided here.

Finally, exemplary ablation description characteristics may further include intracardiac echocardiography (ICE) characteristics, such as, for example, the amount or magnitude of blood flow/cooling of the lesion being formed in the tissue 12, the lesion diameter, and steam bubble density.

Means by which these particular characteristics are monitored are well known in the art, and therefore, will not be described in greater detail.

As briefly discussed above, the ECU 22 is configured to use values of one or more ablation description parameters corresponding to one or more ablation description characteristics (such as those described above) in order to generate and characterize markers 68, and to place the markers 68 onto an image of the tissue 12. More particularly, and as illustrated in FIG. 5, one or more values of one or more ablation description parameters that correspond to one or more ablation description characteristics (such as those described above) are acquired by the ECU 22. Parameters of the ablation description characteristics may include, for example and without limitation, the characteristic itself or the magnitude of the characteristic at a certain point in time or over a certain time interval, the average of the characteristic over a certain time interval, the change or percentage of change in the characteristic over a certain time interval, the maximum and/or minimum of a characteristic over a certain time interval, the magnitude of the combination of two or more characteristics/parameters, and the like.

Figure 6:
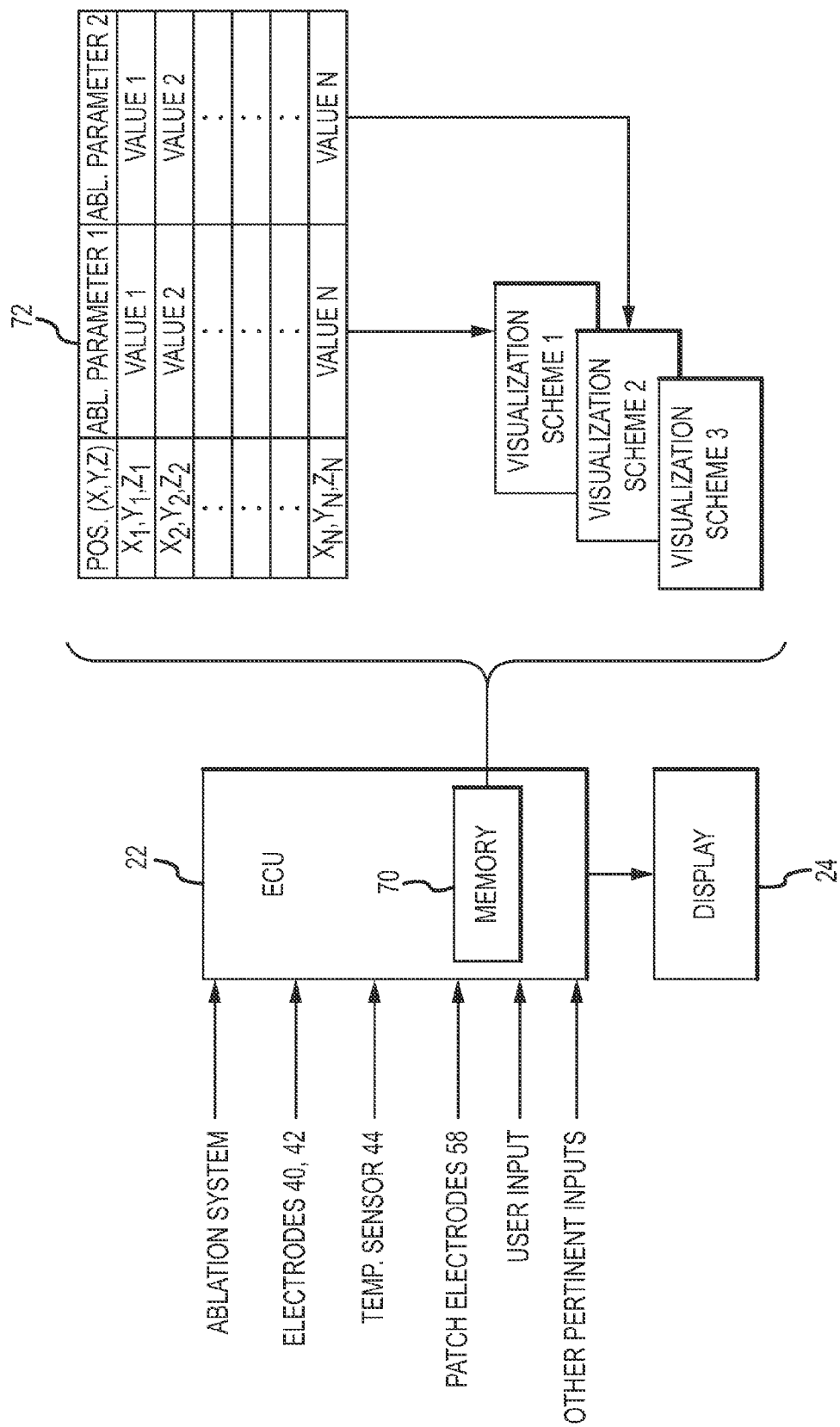
FIG. 6 is block diagram illustrative of an exemplary embodiment of the electronic control unit (ECU) of the system illustrated in FIG. 1.

The ECU 22 may acquire the values of ablation description parameter(s) in a number of ways. For example, and as illustrated in FIG. 6, the ECU 22 may receive input signals representative of values of the parameters from other components within the system 10, such as, for example, the ablation system 18. In another exemplary embodiment, the ECU 22 is coupled to and configured for communication with various sensors and/or electrodes, such as, for example, the electrodes 40, 42, the temperature sensor 44, a complex impedance sensor, and the like, that are configured to generate signals representative of the values of one or more parameters, and therefore, these signals may be inputs of the ECU 22. In this embodiment, the ECU 22 may be configured to sample the values of the parameters at a predetermined sampling rate and to then process the signals accordingly to either determine the value of the parameter represented by the signal, or to make the necessary calculations to resolve the values of the desired parameters (e.g., in the case of a parameter being, for example, an average or change in value over a predetermined time). In any event, the ECU 22 is configured to acquire the value for one or more ablation description parameters that correspond to one or more ablation description characteristics.

With continued reference to FIG. 6, in an exemplary embodiment, the ECU 22 is configured to store some or all of the acquired parameters in, for example, a table 72 that is stored in a memory or storage device that is part of the ECU 22 or accessible thereby (e.g., the memory 70). The ECU 22 may be further configured to determine the position and orientation of the catheter 12 for each parameter using, for example, the techniques described above with respect to the visualization, navigation, and mapping system 20, and to correlate each acquired parameter with position and orientation of the catheter 16. Accordingly, for each parameter, the ECU 22 can determine the position of the catheter 16, and therefore, the location in the tissue 12, to which the parameter corresponds. The ECU 22 may store the position and orientation for each parameter in the table 72 along with the ablation description parameters that correspond to that each particular position and orientation.

In view of the large number of parameters/characteristics that the ECU 22 may be configured to acquire, in an exemplary embodiment, the ECU 22 may be configured to receive instructions from a clinician as to which parameters/characteristics the clinician would like to monitor. Alternatively, the ECU 22 may be pre-programmed with select characteristics/parameters.

Figure 7:
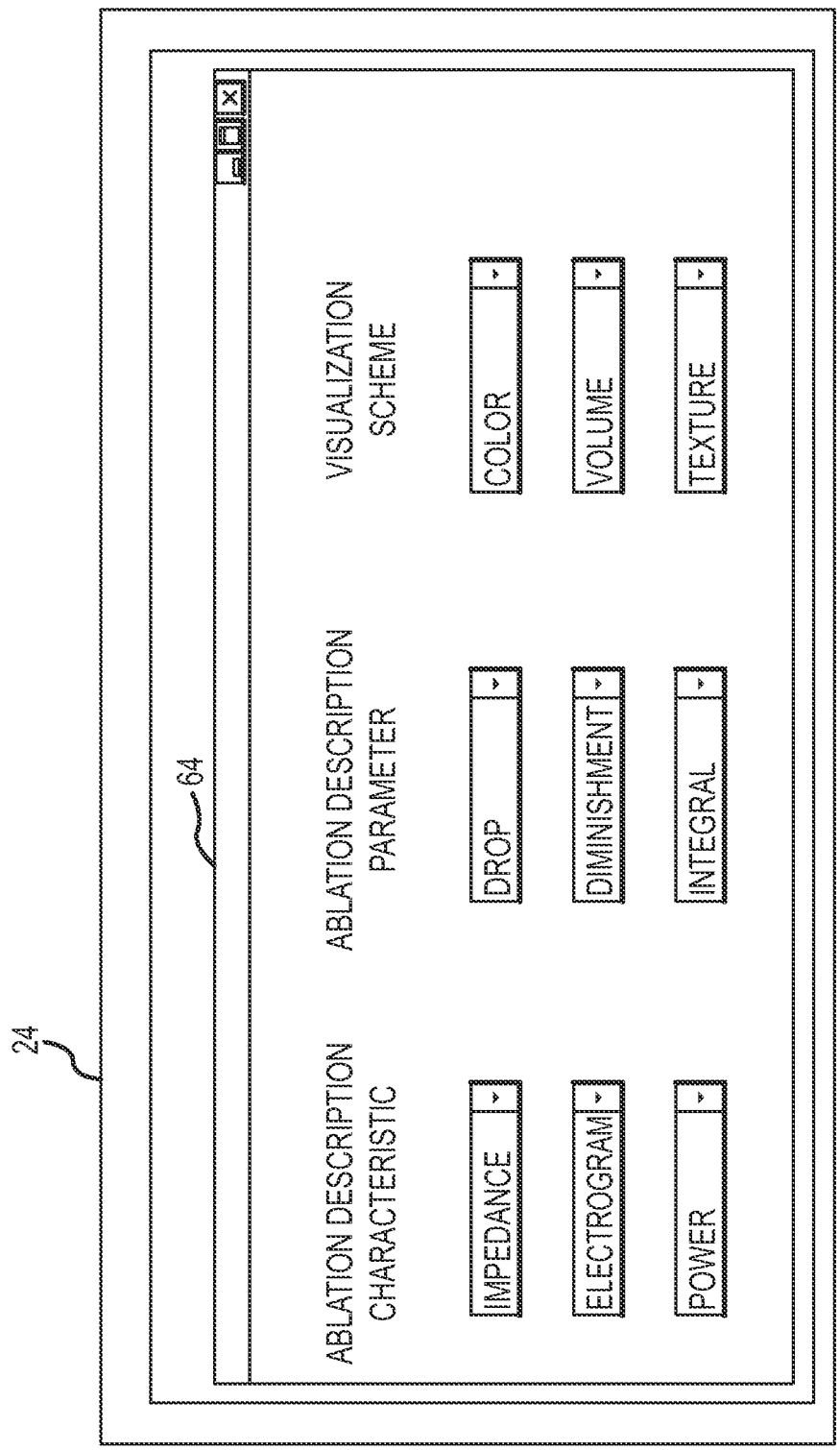
FIG. 7 is another exemplary embodiment of a display device of the system illustrated in FIG. 1 with a graphical user interface (GUI) displayed thereon.

In an embodiment wherein the clinician can select the parameters to be monitored, the GUI 64 may be configured to provide a means by which the clinician can select the characteristics and/or parameters to be monitored. The GUI 64 may present an input screen comprising a plurality of fields in which the clinician may provide his selections. For example, and as illustrated in FIG. 7, the GUI 64 may present the clinician with a first column of drop-down menus that correspond to ablation description characteristics, and a second column of drop-down menus that correspond to ablation description parameters. Accordingly, using an input device 69, such as, for example, a mouse, a keyboard, a touch screen or the like, the clinician may select the characteristic he wants and then the parameter of that selected characteristic.

An alternate embodiment of the GUI 64 is illustrated in FIG. 3, and it provides an alternate means by which the user may select the characteristics and parameters he wishes to monitor. In this embodiment, the user may define additional criteria. For example, the user may define the assessment time interval over which one or more ablation description parameters are monitored. For example, if the clinician is interested in the total power applied to the tissue 12 over a particular time interval, the clinician can enter the desired time interval using the GUI 64.

Similarly, using the GUI 64 illustrated in FIG. 3, for example, the clinician may define a stability radius, which will be described in greater detail below with respect to assessing the stability of the catheter 16. However, in an exemplary embodiment, in addition to using the stability radius to evaluate stability, the ECU 22 may use the stability radius in the characterization of the marker 68. More particularly, the clinician may define the area of the tissue 12 that he wants included in the characterization of the marker 68. For example, if the clinician is interested in the total power applied to a particular location of the tissue and the area of the tissue that is within 5 mm of the location, he can define the stability radius to be 5 mm, and then the ECU 22 will determine the power applied to the current location and the area of the tissue within 5 mm thereof based on current and past acquired values of the power. Similarly, the stability radius and the defined assessment time interval may be used in concert. For example, if the assessment time interval is 20 s and the radius is 5 mm, the ECU 22 will look back 20 s and collect the applied power values for those areas that are within 5 mm of the current location, and then combine them for the total power parameter value. In either example, a marker 68 will then be generated that encompasses the current location and the area within the stability radius. Accordingly, the size of the marker 68 is dependent upon the magnitude of the radius. It will be appreciated that the description above, while limited to the ablation description parameter of total power, applies to the other ablation description characteristics and parameters thereof described herein.

Turning back to FIG. 5, once it is determined which characteristics/parameter(s) is/are to be monitored, whether other criteria (e.g., assessment time interval and radius) are to be taken into consideration, and values for the parameters are acquired by the ECU 22, the ECU 22 is configured to evaluate those the values of the parameter(s) and to generate and characterize a marker (i.e., marker 68) to reflect the values of the acquired parameters.

More particularly, the ECU 22 is configured to associate a visualization scheme with each monitored parameter (See, for example, FIG. 6). Exemplary visualization schemes include, for example and without limitation, color coding schemes, volumizing schemes, texturizing schemes, and translucency schemes. Each visualization scheme comprises a plurality of visual indicators that are used to represent the particular values of the associated parameter. For example, if predicted lesion depth is the monitored parameter and the associated visualization scheme is "color", one color may be assigned to a first depth or range of depths, a second color may be assigned to a second depth or range of depths, etc. Similarly, if the monitored parameter is tissue temperature and the visualization scheme is texture, a first texture may be assigned to a first temperature or temperature range, a second texture may be assigned to a second temperature or temperature range, etc. Accordingly, each visualization scheme comprises a plurality of visual indicators, wherein each indicator corresponds to a certain value or range of values of the parameter with which the visualization scheme is associated. Thus, the ECU 22 is programmed such that each visual indicator is associated with a particular value or range of values for the monitored parameter. Further, because in different applications or procedures the same visualization scheme may be used for different parameters, the ECU 22 is configured and programmed such that for each parameter for which a visualization scheme may be associated, the visual indicators thereof are in turn associated with corresponding particular values or range of values for that parameter. Accordingly, the ECU 22 may be configured to allow each visualization scheme to be used for different parameters.

The ECU 22 may be pre-programmed with the respective parameter/visualization scheme associations, or the ECU 22 may make the associations in response to user inputs. For example, the GUI 64 may provide a means by which the clinician can associate a visualization scheme with a parameter. More particularly, with reference to FIG. 7 and as with the selection of ablation description characteristics and parameters described above, the GUI 64 may present the clinician with a third column of drop-down menus that correspond to available visualization schemes. Accordingly, using the input device 69, such as, for example, a mouse, a keyboard, a touch screen and the like, the clinician may select the visualization scheme he wants for each parameter being monitored.

With continued reference to FIG. 5, once a value for an ablation description parameter of interest has been acquired and a visualization scheme has been associated with the parameter of interest, the ECU 22 is configured to evaluate the parameter value and then assign it a visual indicator of the visualization scheme. More particularly, the ECU 22 is configured to look up the value in a look-up table, for example, to determine which of the visual indicators of the visualization scheme corresponds to the value of the parameter. The ECU 22 is then configured to assign the correct visual indicator to the value. Once a visual indicator has been assigned to the value, the ECU 22 is configured to generate the marker 68 responsive to the assignment of the visual indicator that comprises the visual indicator such that the marker 68 is indicative of the value of the parameter.

In an exemplary embodiment, there may be more than one parameter of interest that the clinician may wish to monitor. In one such embodiment generally illustrated in FIG. 12, the aforedescribed process may be repeated such that the generated marker 68 comprises multiple visual indicators corresponding to the visualization schemes associated with the respective ablation description parameters. For example, one parameter of interest may be associated with a color coding visualization scheme, while another parameter of interest may be associated with a texturizing scheme. In such an embodiment, the generated marker 68 would include both a color coding indicator (e.g., a certain color or shade of color), and also include a particular texture (e.g., smooth, multi-faceted, denser grid, etc., see FIG. 4). Accordingly, one marker may be characterized to be indicative of more than one ablation lesion parameter, thereby providing the clinician with one comprehensive lesion evaluation tool that enables the clinician to monitor and objectively assess many ablation description parameters at one time. In another exemplary embodiment, a visual indicator may be assigned based on the combination of the values of multiple parameters.

With continued reference to FIG. 5, once the marker 68 is generated, the ECU 22 may be further configured to superimpose it onto the image 66. More particularly, the ECU 22 may use the location and orientation of the catheter corresponding to the parameter value(s) to superimpose the marker 68 onto the image at the location to which the parameter(s) correspond. The ECU 22 is further configured to control the display device 24 to display the image 66 with the marker 68 superimposed thereon. Thus, as illustrated, for example, in FIG. 4, the ECU 22 is configured to generate a lesion formation map by generating and characterizing the markers and superimposing them onto the image in the correct locations, and to display the lesion formation map for the clinician to see and use.

In an exemplary embodiment, as an ablation procedure performed on the tissue 12 progresses, the clinician may wish to continuously monitor the ablation description parameter for a particular location in the tissue 12. Accordingly, the marker 68 may be updated as the parameter value changes, and therefore, the characterization of the marker 68 may change as the ablation procedure progresses (e.g., the color of the marker may get lighter, darker, or change colors altogether; the texture may change from smooth to faceted, and vice versa; the marker may become more or less translucent; the volume of the marker may increase or decrease, etc.). Therefore, the ECU 22 may be configured to monitor the parameter at a particular location and update (i.e., re-generate) the marker 68 with each acquired value or at another predetermined rate.

The ECU 22 may generate, characterize, and place the marker 68 onto the image 66 automatically, or may do so in response to a user input to do so. For example, for each sampled or calculated parameter value, the ECU 22 may be configured to automatically generate and characterize a marker, or update an existing marker, and also cause the marker to be placed on the image 66 in the correct location. Alternatively, the ECU 22 may be configured to generate, characterize, and place the marker on the image only after the parameter value meets, exceeds, or falls below a certain predetermined threshold. In another exemplary embodiment, however, the ECU 22 is configured to sample or calculate the value of the parameter at a certain predetermined rate, and then, when instructed to do so by an input signal generated by the user of the system 10 inputting instructions into a user input device (e.g., input device 69), generate and characterize a marker 68 and cause it to be placed on the image 66 in the correct location. User input devices may include, for example, the GUI 64 or another input device 69 that may or may not be associated with the GUI 64, such as, for example, a key board, a touch screen, a key pad, a mouse, a button associated with the catheter handle 32, or other like devices. Accordingly, the ECU 22 may be configured to automatically generate, characterize, and place a marker onto the image, or be configured to generate, characterize, and place a marker onto the image in response to an input signal. In either instance, in an exemplary embodiment, the ECU 22 is further configured to control the display device 24 to display the image 66 with the marker(s) 68 disposed thereon.

In an exemplary embodiment, and as illustrated in FIG. 4, the ECU 22 may be further configured to cause the ablation description parameters corresponding to a particular marker to be displayed on, for example, the display device 24. More particularly, using a user input device, such as, for example, the GUI 64, the clinician may be permitted to select a particular marker 68 displayed on the display device 24, and to then cause the values of the monitored ablation parameters to be displayed. For example and as illustrated in FIG. 4, the user may select a marker of interest (e.g., marker A, B, or C), and then the ECU 22 is configured to display the information corresponding to that marker on the display device 24, and GUI 64, in particular. Accordingly, the ECU 22 is configured to access the table 72 in which the values of the ablation description parameters are stored, acquire the values that correspond to the selected marker, and then display them on the display device 24.

In an exemplary embodiment, the ECU 22 may compensate for motion occurring within the region in which the catheter 16 is disposed in the generation, characterization, and placement of markers 68. Motion may be caused by, for example, cyclic body activities, such as, for example, cardiac and/or respiratory activity. Accordingly, the ECU 22 may incorporate, for example, cardiac and/or respiratory phase into the marker characterization, generation, and placement.

For example, in one embodiment, the ECU 22 may be configured to employ time-dependent gating in an effort to increase accuracy of the characterization and/or placement of the marker 68. In general terms, time-dependent gating comprises monitoring a cyclic body activity and generating a timing signal, such as an organ timing signal, based on the monitored cyclic body activity. The organ timing signal may be used for phase-based characterization and placement, thereby resulting in more accurate lesion assessment mapping throughout an ablation procedure and the different phases of the cyclic activity.

For the purposes of clarity and brevity, the following description will be limited to the monitoring of the cardiac cycle. It will be appreciated, however, that other cyclic activities (e.g., respiratory activity, combination of cardiac and respiratory activities, etc.) may be monitored in similar ways and therefore remain within the spirit and scope of the present invention. Accordingly, in an exemplary embodiment, the system 10 includes a mechanism to measure or otherwise determine a timing signal of a region of interest of the patient's body, which, in an exemplary embodiment, is the patient's heart, but which may also include any other organ that is being evaluated. The mechanism may take a number of forms that are generally known in the art, such as, for example, a conventional electro-cardiogram (ECG) monitor. A detailed description of a ECG monitor and its use/function can be found with reference to U.S. Patent Publication No. 2010/0168550 entitled "Multiple Shell Construction to Emulate Chamber Contraction with a Mapping System," which is incorporated herein by reference in its entirety.

Figure 8:
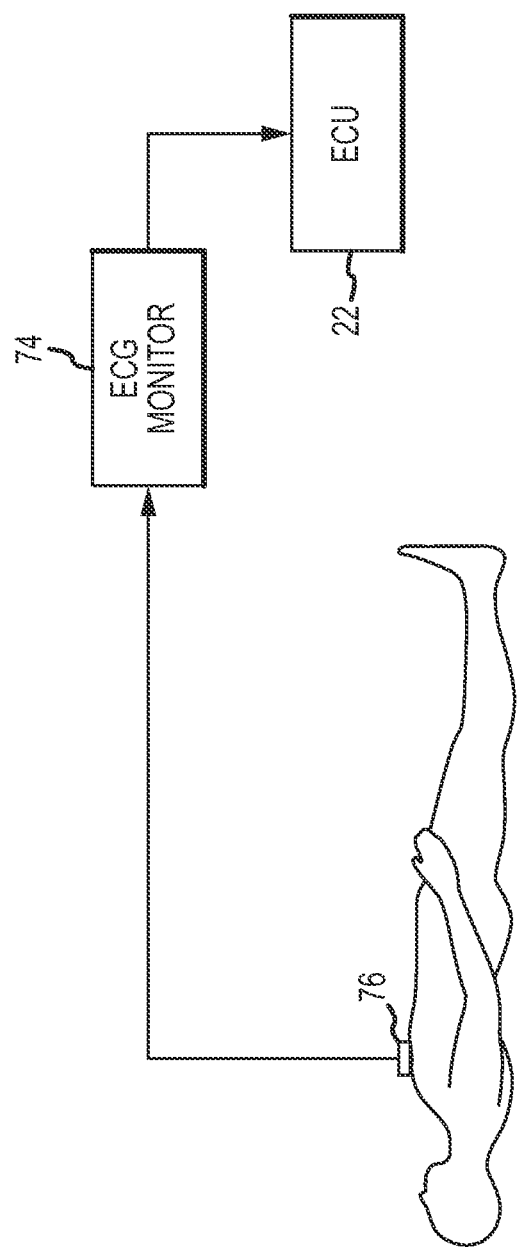
FIG. 8 is a schematic and diagrammatic view of a portion of the system illustrated in FIG. 1 used in connection with time-dependent gating.

With reference to FIG. 8, in general terms, an ECG monitor 74 is provided that is configured to continuously detect an electrical timing signal of the patient's heart through the use of a plurality of ECG electrodes 76, which may be externally-affixed to the outside of a patient's body. The timing signal generally corresponds to the particular phase of the cardiac cycle, among other things. In another exemplary embodiment, rather than using an ECG to determine the timing signal, a reference electrode or sensor positioned in a fixed location in the heart may be used to provide a relatively stable signal indicative of the phase of the heart in the cardiac cycle (e.g., placed in the coronary sinus). In still another exemplary embodiment, a medical device, such as, for example, a catheter having an electrode may be placed and maintained in a constant position relative to the heart to obtain a relatively stable signal indicative of cardiac phase. Accordingly, one of ordinary skill in the art will appreciate that any number of known or hereinafter developed mechanisms or techniques, including but not limited to those described above, may be used to determine a timing signal.

Once the timing signal, and therefore, the phase of the patient's heart, is determined, the position information corresponding to the position of the positioning electrode 42 (which, in an exemplary embodiment, may alternatively comprise a magnetic sensor (e.g., coil), and therefore, the ablation description parameter values corresponding to the position information, may be segregated or grouped into a plurality of sets based on the respective phase of the cardiac cycle during or at which each position was collected. Once the position and ablation description parameter information is grouped, the ECU 22 is configured to generate a lesion formation map for one or more phases of the cardiac cycle comprising markers 68 characterizing values for ablation description parameters collected during each respective phase of the cycle. Because the timing signal is known, as each subsequent position of the positioning electrode 42 and values for ablation description parameters corresponding to that position are acquired, the position and parameter values are tagged with a respective time-point in the timing signal and grouped with the appropriate previously recorded position and parameter information. The subsequent positions and values may then be used to generate a lesion formation map for the phase of the cardiac cycle during which the position and parameter values were collected/acquired.

Once a lesion formation map is generated for each phase of the cardiac cycle, the lesion formation map corresponding to the current phase of the timing signal may be presented to the user of the system 10 at any time. In an exemplary embodiment, the ECU 22 may be configured to play-back the lesion formation maps (e.g., sequentially reconstructed and displayed on the display 24) in accordance with the real-time measurement of the patient's ECG. Therefore, the user may be presented with an accurate real-time lesion formation map regardless of the phase of the cardiac cycle. Accordingly, it will be understood and appreciated that the lesion formation map for each phase may be stored in a memory or storage medium, such as, for example, the memory 70, that is either part of or accessible by the ECU 22 such that the ECU 22 may readily obtain, render, and/or display the appropriate lesion formation map.

Figure 9:
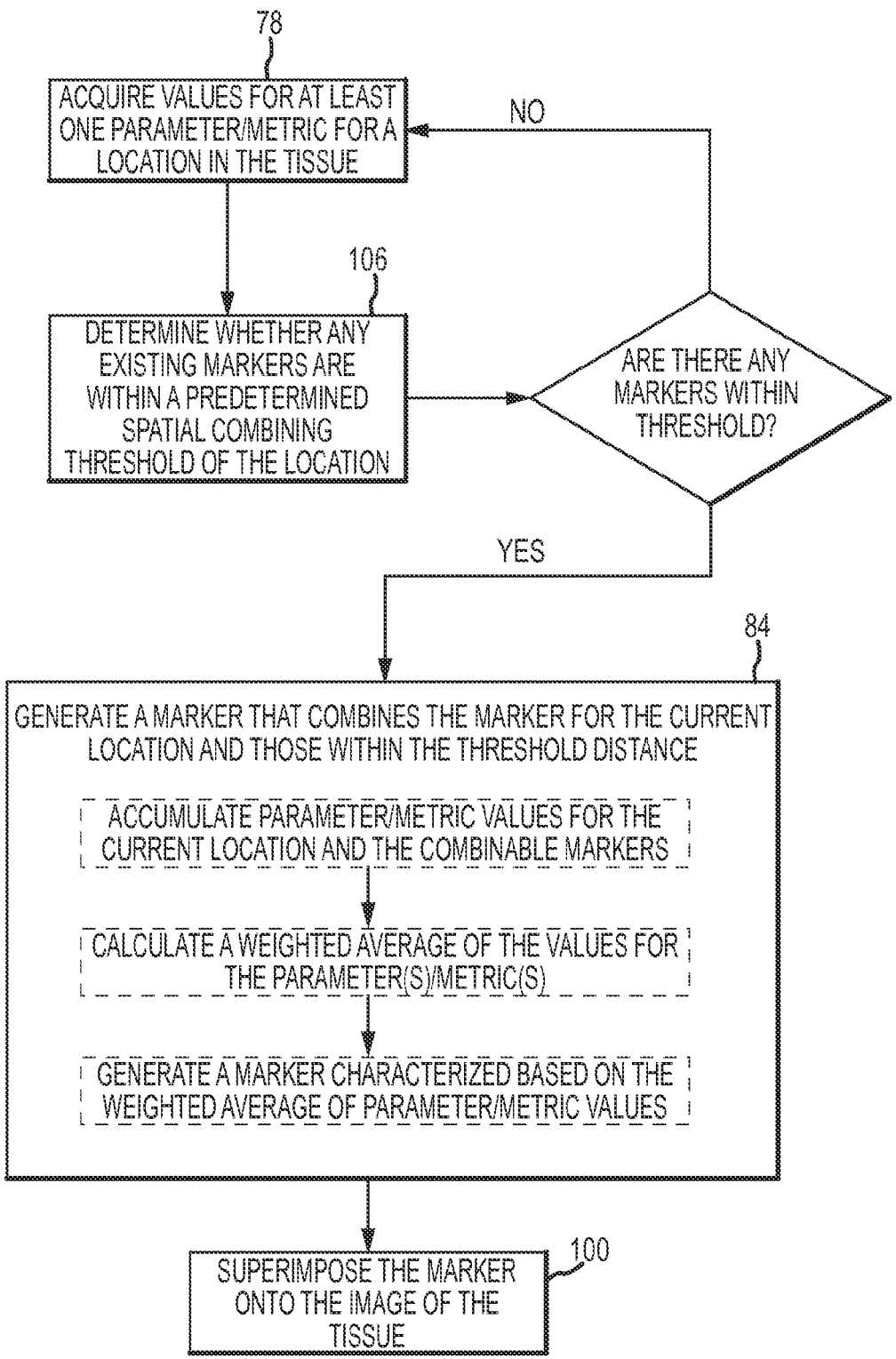
FIG. 9 is a flow chart illustrative of an exemplary embodiment of a method of combining lesion markers in accordance with the present teachings

In an exemplary embodiment, the ECU 22 may be further configured to combine markers 68 that are disposed within a predetermined distance from each other so as to create a contiguous lesion marker. More particularly, and with reference to FIG. 9, the ECU 22 may be configured to acquire parameter values for a particular location, and then determine whether any markers are within a predetermined distance of the location. If any markers are within the predetermined distance, the ECU 22 may generate a marker that combines a marker for the currently evaluated location with those existing markers 68 falling within the predetermined distance of the current location, thereby creating a larger, contiguous marker 68. For example, in one embodiment, the ECU 22 is either pre-programmed with a spatial lesion combining threshold, or is configured such that the clinician can define the threshold using, for example, the GUI 64. The spatial lesion combining threshold is the maximum distance a currently evaluated location and adjacent markers 68 can be from each other and be automatically combined. Accordingly, if one or more markers 68 are disposed less than the threshold distance from the currently evaluated location, the markers 68 may be combined with a marker for the currently evaluated location; otherwise, they are not. If one or more markers 68 meet the combination criteria, in an exemplary embodiment, the values of the ablation description parameters used to characterize the markers are accumulated for both the currently evaluated location and the combinable markers 68. Once the values are accumulated, a new lesion marker 68 is generated and characterized based on the weighted average of the respective parameter values. The new marker 68 is then superimposed onto the image 66. Alternatively, in an instance wherein two or more markers would overlap (i.e., a marker for the currently evaluated location and adjacent markers 68), the area(s) of overlap between each of the marker for the currently evaluated location and the combinable markers 68 may be characterized such that the overlapping area has a different visual indicator than the non-overlapping portions (e.g., a darker shade or different color in an instance wherein the visualization scheme is a color coding scheme).

In an exemplary embodiment, the ECU 22 is further configured to assess the stability of the catheter 16, and the electrodes (e.g., positioning sensors, positioning electrodes, etc.) thereof, and to use the stability of the catheter 16 in the characterization and/or placement of the marker 68. Accordingly, the marker 68 may be characterized to reflect the stability of the catheter 16 in the same way described above with respect to the ablation description parameters (i.e., a value of a position signal metric is acquired or calculated representative of the stability of the catheter and may be used in the characterization of the marker 68), may be used in the calculation or acquisition of the ablation description parameter value (i.e., the only parameter values used to characterize the marker or to calculate a parameter value of interest are those acquired when the catheter is "stable"), and/or may be used by the ECU 22 to determine whether or not the marker 68 should be placed on the image 66 (i.e., if the catheter meets certain stability criteria, the marker is placed on the image, while if the catheter does not meet the criteria, the marker is not placed on the image).

Figure 10:
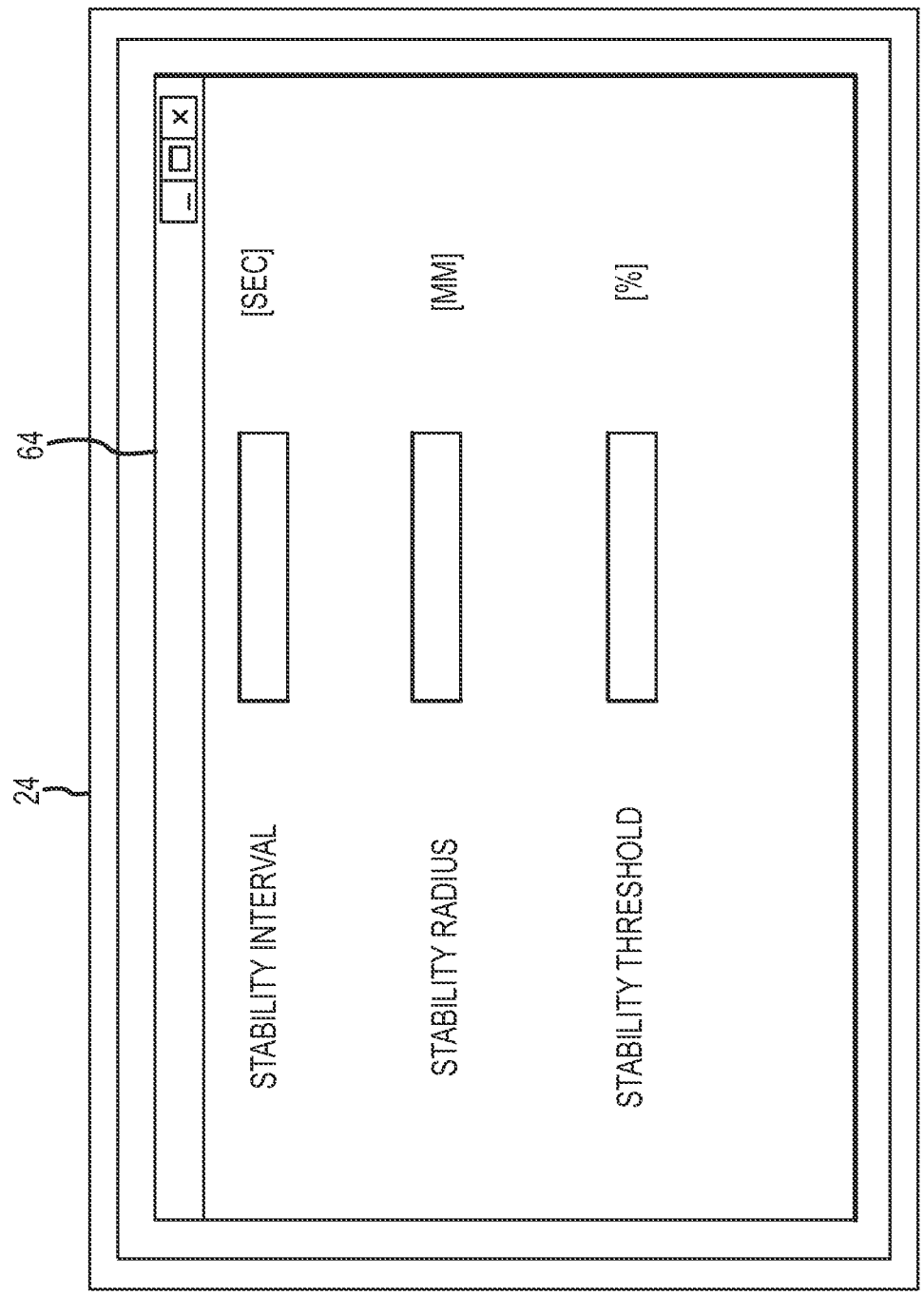
FIG. 10 is another exemplary embodiment of a display device of the system illustrated in FIG. 1 with a graphical user interface (GUI) displayed thereon.
Figure 11A:
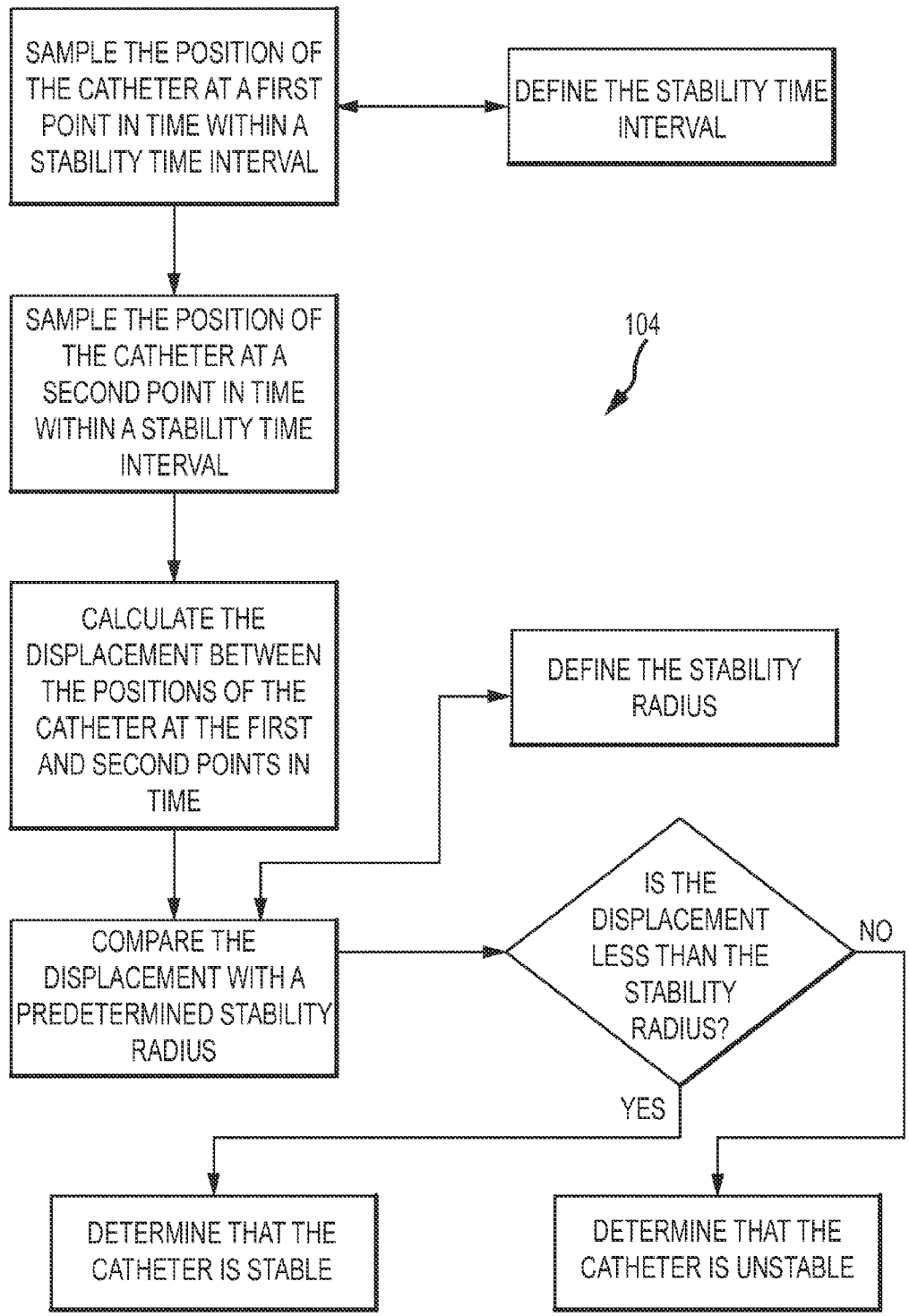
FIGS. 11a-11c are flow charts illustrative of exemplary embodiments of methodologies for assessing the stability of a positioning electrode, and therefore, catheter associated therewith.

The stability may be determined in any number of ways. In one exemplary embodiment, the ECU 22 is configured to assess the displacement of the catheter 16, and therefore, one or more electrodes thereof, over a predetermined stability time interval. The ECU 22 may be pre-programmed with a stability time interval, or the interval may be defined by the user or clinician using an input device, such as, for example, the GUI 64, an exemplary embodiment of which is illustrated in FIG. 10. Accordingly, the ECU 22 is configured to sample the position of the catheter 16 using the techniques described in great detail above at a predetermined rate over the stability time interval, and to then calculate a displacement between each sampled position and one or more positions previously acquired during the stability time interval. For example and as illustrated in FIG. 11a, the ECU 22 acquires a first position of a positioning sensor, which may include, for example, a positioning electrode (e.g., the positioning electrode 42 or another positioning electrode of the catheter 16) or, alternatively, a magnetic sensor (e.g., coil), at a first time during the stability time interval. For purposes of illustration and clarity only, the description below of the stability determination/assessment will be with respect to a positioning sensor comprising the positioning electrode 42. It will be appreciated, however, that positioning sensors other than positioning electrodes or the positioning electrode 42 remain within the spirit and scope of the present disclosure. Accordingly, after the ECU 22 acquires the first position of the positioning electrode 42, it stores the position in, for example, a memory or storage medium that is part of or accessible by the ECU 22 (e.g., the memory 70). In an exemplary embodiment, the ECU 22 acquires a second position of the electrode 42 at a second point in time during the defined stability time interval, and then calculates the displacement between the two positions. The ECU 22 then acquires a third position of the electrode 42 at a third point in time in the stability time interval, and then calculates the displacement between it and the first position.

In an exemplary embodiment, the ECU 22 is further configured to compare each calculated displacement with a predetermined stability radius and to determine, based on the comparison, whether the catheter 16 is stable. More specifically, if the displacement meets or is less than the stability radius, a determination can be made that the catheter 16 is stable. If, however, the displacement is above the stability radius, a determination can be made that the catheter 16 is not stable. As with the stability time interval, the ECU 22 may be pre-programmed with a stability radius, or the radius may be defined by the user or clinician using an input device, such as, for example, the GUI 64 illustrated in FIG. 10. This stability assessment may be performed for each acquired position, or at some other predetermined rate, such as, for example, after a certain amount of time has elapsed, or after a certain number of positions have been acquired (e.g., stability is assessed every fifth sample, for example).

In an exemplary embodiment, in addition to the stability time interval and the stability radius, the stability may be assessed using the additional criteria of a stability tolerance. The stability tolerance represents the percentage of displacements that must be within the stability radius for the catheter to be deemed stable. Accordingly, if the stability tolerance is 90%, then 90% of the displacements over the stability interval must be within the stability radius for the catheter to be deemed stable. As with both the stability time interval and the stability radius, the ECU 22 may be pre-programmed with a stability tolerance, or the tolerance may be defined by the user or clinician using an input device, such as, for example, the GUI 64 illustrated in FIG. 10. Accordingly, in an exemplary embodiment illustrated, for example, in FIG. 11b, a series of displacements are calculated over the stability interval and some or all of them are compared with the stability radius. The ECU 22 then determines what percentage of the calculated displacements were within the stability radius, and compares that percentage to the stability tolerance. If the percentage meets or exceeds the tolerance, then the catheter may be deemed to be stable. On the other hand, if the percentage is less than the tolerance, then the catheter may be deemed to be unstable.

Figure 11B:
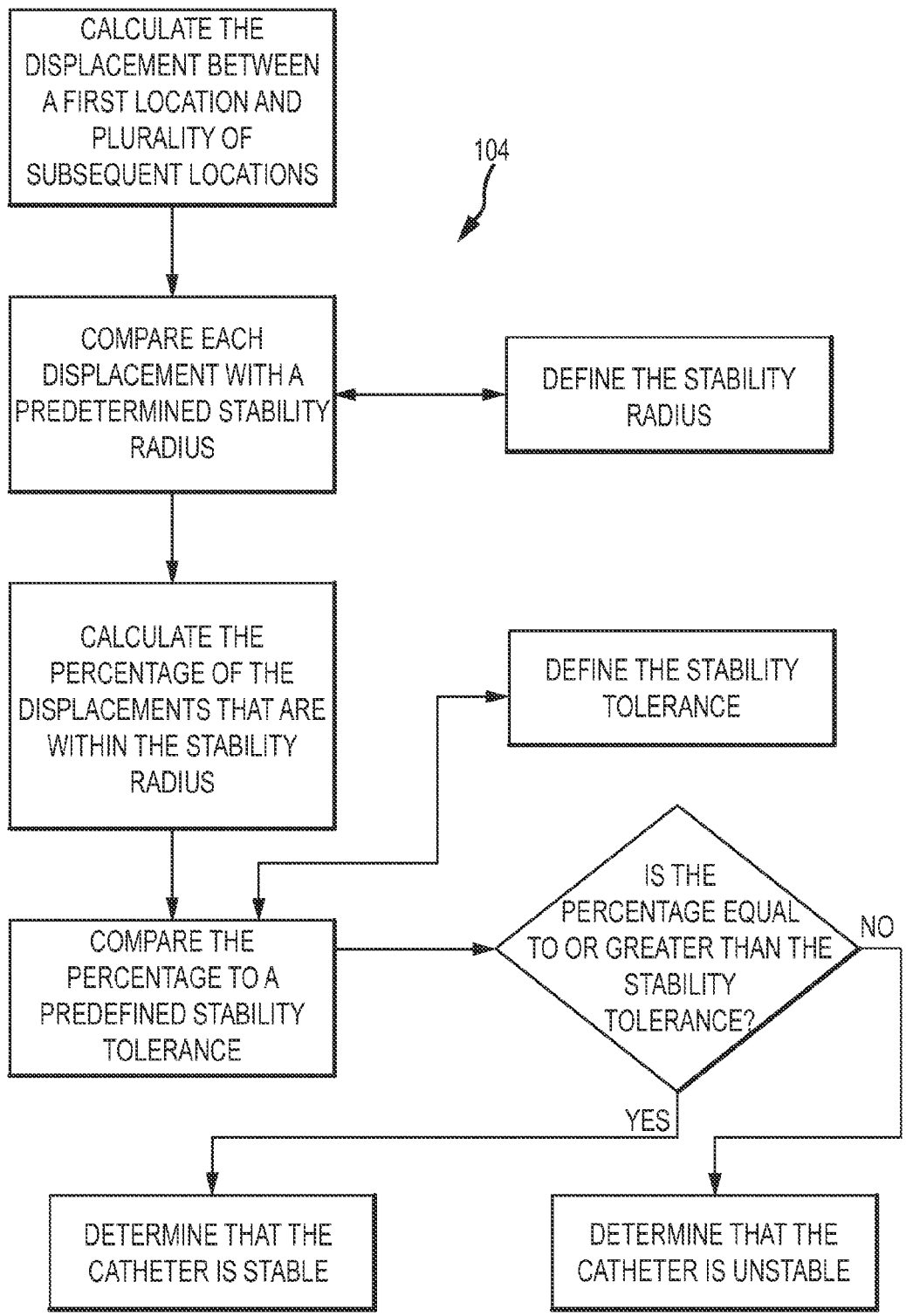
Figure 11C:
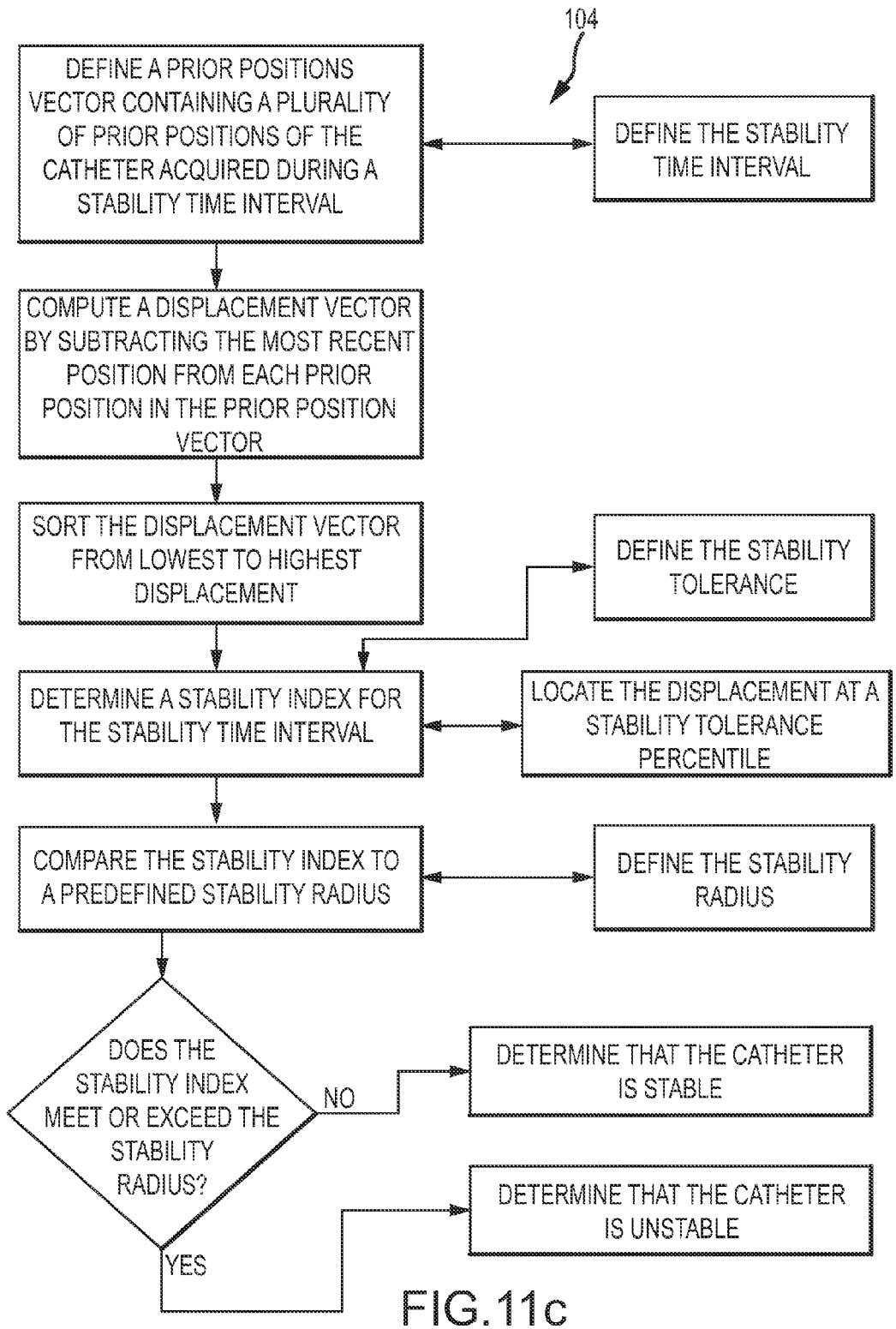

In another exemplary embodiment illustrated, for example, in FIG. 11c, the ECU 22 is configured to assess the stability of the catheter 16 by computing a stability index. The ECU 22 may take into account the stability time interval, the stability radius, and the stability tolerance in this assessment, and the assessment may be a real time running assessment.

More particularly, in an exemplary embodiment, the ECU 22 is configured to define a prior positions vector that contains some or all of the positions that are acquired by the ECU 22 within the most recent stability time interval (i.e., if the stability time interval is 20 s, all of the positions acquired within the past 20 s). The ECU 22 is also configured to compute a displacement vector by subtracting the most recent position from each position in the previous positions vector. Once the displacement vector is computed, the ECU 22 is configured to sort the displacement vector. In an exemplary embodiment, the displacement vector is sorted from the lowest displacement to the highest displacement. Using the sorted displacement vector, the ECU 22 is configured to then determine the stability index for the stability time interval. In one exemplary embodiment, the stability index is defined as the displacement at the stability tolerance percentile. Accordingly, the ECU 22 is configured to identify the displacement in the displacement vector that corresponds to the stability tolerance, and to then define the stability index to be the corresponding displacement. For example, if there are ten (10) displacements in the displacement vector and the stability tolerance is 90%, the ECU 22 would locate the ninth displacement in the sorted displacement vector by starting at the lowest displacement in the vector and counting upwards in the vector until the ninth displacement is reached. If the displacement at the ninth position in the sorted displacement vector is 3 mm, then the ECU 22 defines the stability index to be 3 mm. Once the stability index is defined, in an exemplary embodiment, the stability is assessed by comparing the stability index to the stability radius in the same manner described above. Accordingly, if the stability index exceeds (or in some instances meets or exceeds) the stability radius, the ECU 22 may determine that the catheter 16 is not stable. Alternatively, if the stability index falls below (or in some instances meets or falls below) the stability radius, the ECU 22 may determine that the catheter is stable.

As with the characterization of the markers 68 based on ablation description characteristics/parameters, in an exemplary embodiment, the ECU 22 may compensate for motion occurring within the region in which the catheter 16 is disposed in the stability assessment. As described above, motion may be caused by, for example, cyclic body activities, such as, for example, cardiac and/or respiratory activity. Accordingly, the ECU 22 may incorporate, for example, cardiac and/or respiratory phase into the stability assessment.

For example, in one embodiment, the ECU 22 may be further configured to employ time-dependent gating in an effort to increase accuracy of the stability assessment. In general terms, time-dependent gating comprises monitoring a cyclic body activity and generating a timing signal, such as an organ timing signal, based on the monitored cyclic body activity. The organ timing signal may be used for phase-based stability assessment, thereby resulting in more accurate stability assessment throughout an ablation procedure and the different phases of the cyclic activity.

For the purposes of clarity and brevity, the following description will be limited to the monitoring of the cardiac cycle. It will be appreciated, however, that other cyclic activities (e.g., respiratory activity, combination of cardiac and respiratory activities, etc.) may be monitored in similar ways and therefore remain within the spirit and scope of the present invention. Accordingly, in an exemplary embodiment, the system 10 includes a mechanism to measure or otherwise determine a timing signal of a region of interest of the patient's body, which, in an exemplary embodiment, is the patient's heart, but which may also include any other organ that is being evaluated. The mechanism may take a number of forms that are generally known in the art, such as, for example, a conventional electro-cardiogram (ECG) monitor. A detailed description of a ECG monitor and its use/function can be found with reference to U.S. Patent Publication No. 2010/0168550 entitled "Multiple Shell Construction to Emulate Chamber Contraction with a Mapping System," which is incorporated herein by reference in its entirety.

With reference to FIG. 8, in general terms, an ECG monitor 74 is provided that is configured to continuously detect an electrical timing signal of the patient's heart through the use of a plurality of ECG electrodes 76, which may be externally-affixed to the outside of a patient's body. The timing signal generally corresponds to the particular phase of the cardiac cycle, among other things. In another exemplary embodiment, rather than using an ECG to determine the timing signal, a reference electrode or sensor positioned in a fixed location in the heart may be used to provide a relatively stable signal indicative of the phase of the heart in the cardiac cycle (e.g., placed in the coronary sinus). In still another exemplary embodiment, a medical device, such as, for example, a catheter having an electrode may be placed and maintained in a constant position relative to the heart to obtain a relatively stable signal indicative of cardiac phase. Accordingly, one of ordinary skill in the art will appreciate that any number of known or hereinafter developed mechanisms or techniques, including but not limited to those described above, may be used to determine a timing signal.

Once the timing signal, and therefore, the phase of the patient's heart, is determined, the position information corresponding to the position of the positioning electrode 42 may be segregated or grouped into a plurality of sets based on the respective phase of the cardiac cycle during (or at which) each position was collected. Once the position information is grouped, the ECU 22 is configured to determine the stability of the catheter 16 for one or more phases of the cardiac cycle in the manner described above using only those positions of the electrode 42 that were collected during that particular phase for which the stability is being assessed. Because the timing signal is known, as each subsequent position of the positioning electrode 42 is acquired, the position is tagged with a respective time-point in the timing signal and grouped with the appropriate previously recorded position information. The subsequent positions may then be used to assess the stability of the catheter 16 for the phase of the cardiac cycle during which the position was collected. If desired, the overall stability over multiple phases of the cyclic activity may also be determined. For example, if the catheter 16 is determined to be unstable during any one phase of the cyclic activity, the ECU 22 may deem the catheter 16 to be unstable. In another exemplary embodiment wherein the stability is assessed using the stability index described above, the smallest stability index of any of the phases may be compared to the stability radius to determine stability. Accordingly, stability may be assessed on a phase-by-phase basis, or on a combination of phases basis.

In another exemplary embodiment, in addition to assessing stability using the criteria and techniques described above, the ECU 22 is configured to assess the stability of the catheter 16 by taking into account the length of time that the stability criteria are met. More particularly, the ECU 22 may be configured to determine the whether stability criteria is met using the techniques described above, to calculate the length of time that the catheter 16 is continuously deemed to be stable, to compare the calculated length of time with a predetermined time value (i.e., stability hold), and to determine, based on the comparison, where the catheter can be said to be stable. If the catheter 16 is stable for a period of time that meets or exceeds the stability hold time value, the ECU 22 may determine that the catheter is stable. If, on the other hand, the catheter is stable for a time less than the stability hold time value, but then becomes unstable prior to the threshold being met, the ECU 22 may determine that the catheter is unstable, and as a result, the stability time resets. The ECU 22 may be pre-programmed with the time value, or the time value may be defined by the user or clinician using an input device, such as, for example, the GUI 64.

As briefly described above, once the stability of the catheter 16 has been assessed or determined, it may be used in the placement of the marker 68 onto the image 66 and/or to characterize the marker 68.

With respect to the placement of the marker 68, the ECU 22 may be configured to place the marker 68 onto the image 66 only after it determines that the catheter 16 is stable (i.e., meets the defined stability criteria). Accordingly, if the ECU 22 determines that the catheter meets certain stability criteria, and therefore, is stable, the ECU 22 will superimpose the generated marker 68 onto the image 66. Conversely, if the ECU 22 determines that the catheter 16 does not meet certain stability criteria, and therefore, is unstable, the ECU 22 will not superimpose the generated marker 68 onto the image 66. In another exemplary embodiment, rather than the ECU 22 generating the marker 68, the marker 68 is generated elsewhere and is obtained by the ECU 22. Accordingly, it will be appreciated that the marker 68 may be acquired by the ECU 22 by either generating the marker 68 itself, or by obtaining it from another component that is in communication with the ECU 22. The description above relating to the use of the stability in the placement of the marker 68 applies to either instance.

With respect to the use of the stability in the characterization of the marker 68, the stability may be used in a number of ways. In one exemplary embodiment, the stability may be used to determine whether certain ablation description parameters should be used in the characterization of the marker 68. More particularly, if values of ablation description parameters are acquired at least in part by the catheter 16, and electrodes mounted thereon, in particular, the ECU 22 may be configured to acquire or use the values of those parameters only if the catheter 16 was deemed to be stable when the values were acquired. Accordingly, if the catheter is deemed to be stable, or was deemed to be stable when the values were acquired, the values of the ablation description parameters will be acquired, used, or retained. Otherwise, if the catheter is deemed to be unstable, or was unstable when the values were acquired, the values of the ablation description parameters will not be acquired or used, and if already acquired, will be discarded. Accordingly, the stability determination may be taken into account in the characterization of the marker 68.

In another exemplary embodiment, the marker 68 may be characterized based on the stability determination or assessment. In such an embodiment, a position signal metric derived from the position of the positioning electrode 42 is acquired. The position signal metric may take a variety forms depending on the technique used to assess the stability. For example, in an embodiment wherein the displacement between two positions is calculated and then compared to a predetermined stability radius, the position signal metric is the displacement value. Alternatively, in an embodiment wherein stability is assessed by calculating multiple displacements between positions, comparing each displacement to a stability radius, determining the percentage of displacements that are within the stability radius, and then comparing that percentage to a stability tolerance, the position signal metric is the percentage of displacements that are within the stability radius. In still another embodiment wherein a stability index is calculated and compared to a stability radius, the stability index is the position signal metric. Accordingly, any number of values may be used to define the position signal metric.

As with the ablation description parameters described above, once it is determined which position signal metric is/are to be monitored, the ECU 22 is configured to evaluate those particular metric(s) and to generate and characterize a marker (i.e., marker 68) to reflect the values of the acquired metric. More particularly, the ECU 22 is configured to associate a visualization scheme with each monitored metric. Exemplary visualization schemes include, for example and without limitation, those described above, namely, color coding schemes, volumizing schemes, texturizing schemes, and translucency schemes. When used with position signal metrics, the visualization schemes may comprise one or more visual indicators that are used to represent the particular values of the associated metric.

In an exemplary embodiment, the visualization schemes used with the position signal metrics may include one visual indicator that is indicative of the catheter 16 being stable, or alternatively unstable, at a particular location (e.g., the marker may be colored green if the catheter was stable). In another exemplary embodiment, the visualization schemes may include two visual indicators—one for indicating that the catheter is stable at a particular location, the other for indicating that the catheter is unstable (e.g., the marker may be colored green if the catheter was stable, and red if unstable). In each of these embodiments, the determination as to stability would be based on the value of the position signal metric. In still another exemplary embodiment, the visualization schemes may include a plurality of visual indicators that are indicative of the actual value of the metric, or the degree of stability based on the value of the metric (e.g., different colors may correspond to different degrees of stability or values of the metric). Accordingly, the ECU 22 is programmed such that the visual indicators of the visualization scheme are associated with a particular position signal metric value or stability determination. Further, because in different applications or procedures one visualization scheme may be used for different metrics, the ECU 22 is configured and programmed such that for each metric for which a visualization scheme may be associated, the visual indicators of these schemes are in turn associated with a value or stability determination. Accordingly, the ECU 22 may be configured to allow each visualization scheme to be used for different metrics.

The ECU 22 may be pre-programmed with the respective metric/visualization scheme associations, or the ECU 22 may make the associations in response to user inputs in the same manner described above with respect to the association of visualization schemes with ablation description parameters. For example, the GUI 64 may provide a means by which the clinician can associate a visualization scheme with a metric. Accordingly, using the input device 69, such as, for example, a mouse, a keyboard, a touch screen and the like, the clinician may select the visualization scheme he wants for each metric being monitored.

With reference to FIG. 5, once a value for a position signal metric of interest has been acquired and a visualization scheme has been associated therewith, the ECU 22 is configured to evaluate the value and then assign it a visual indicator of the visualization scheme. More particularly, the ECU 22 may be configured to process the value as described above to determine the stability of the catheter, and to then look up in a look-up table, for example, the visual indicator to be used for that stability determination. Alternatively, the ECU 22 may be configured to look up the value in a look-up table, for example, to determine which of the visual indicators corresponds to the value of the metric. The ECU 22 is then configured to assign the correct visual indicator. Once a visual indicator has been assigned, the ECU 22 is configured to generate the marker 68 responsive to the assignment of the visual indicator that comprises the visual indicator such that the marker 68 is indicative or representative of the value of the metric.

In an exemplary embodiment, there may be more than one metric of interest that the clinician may wish to monitor. In such an embodiment, the aforedescribed process may be repeated such that the generated marker 68 comprises multiple visual indicators corresponding to the visualization schemes that are associated with the respective position signal metrics. For example, one metric of interest may be associated with a color coding visualization scheme, while another metric of interest may be associated with a texturizing scheme. In such an embodiment, the generated marker 68 would include both a color coding indicator (e.g., a certain color or shade of color), and also include a particular texture (e.g., smooth, multi-faceted, etc.). Accordingly, one marker may be characterized to be indicative of more than one position signal metric. Similarly, there may be both ablation description parameters and position signal metrics of interest that the clinician may wish to monitor. The description above applies to this situation as well.

As with the embodiment wherein the marker 68 is characterized based on ablation description parameters, once the marker 68 characterized by position signal metrics (i.e., stability) is generated, the ECU 22 may be further configured to superimpose it onto the image 66. Additionally, as the ablation procedure progresses, the marker 68 may be updated as the position signal metric changes. The descriptions set forth above with respect to both the placement of markers 68 characterized by ablation description parameters, and the updating of the markers 68 over time apply here with equal force and are incorporated herein by reference. Therefore, these descriptions will not be repeated here. Additionally, as with the marker characterized by ablation description parameters, the marker 68 characterized by the position signal metric may be generated, characterized, and placed onto the image 66 automatically, or may do so in response to a user input to do so. The description set forth above with respect to this aspect applies here with equal force and is incorporated herein by reference. Therefore, this description will not be repeated here.

It will be appreciated that in addition to the structure of the system 10 described above, another aspect of the present disclosure is a method for presenting information representative of lesion formation in tissue during an ablation procedure. In an exemplary embodiment, and as described above, the ECU 22 of the system 10 is configured to perform the methodology. However, in other exemplary embodiments, the ECU 22 is configured to perform some, but not all, of the methodology. In such an embodiment, another electronic control unit or processor that is part of the system 10, or that is configured for communication with the system 10, and the ECU 22 thereof, in particular, is configured to perform some of the methodology.

In either instance, and with reference to FIG. 5, in an exemplary embodiment, the method includes a step 78 of acquiring a value for at least one of an ablation description parameter and a position signal metric corresponding to a location in the tissue 12, wherein the position signal metric is derived from a portion of the positioning electrode 42 of the catheter 16.

The method may further include a step 80 of evaluating the acquired value. This may entail, for example, comparing the value to a predetermined threshold or looking up the value in a look-up table for purposes that will be described in greater detail below, such as, for example, the assignment of a visual indicator to the value.

In a step 82, a visual indicator of a visualization scheme associated with the ablation description parameter or position signal metric corresponding to the acquired value is assigned to the acquired value. The method further includes a step 84 of generating a marker 68 responsive to the evaluation of the value and the assignment of the visual indicator. As described above, the marker 68 comprises the visual indicator assigned to the value such that the marker is indicative of the acquired value.

In an exemplary embodiment, the value acquired in the acquiring step 78 is a first value, and the visual indicator assigned in the assigning step 82 is a first visual indicator. In this embodiment, the method further includes a step 86 of acquiring a second value for the ablation description parameter or the position signal metric. The method still further includes a step 88 of evaluating the second value, and a step 89 of assigning a second visual indicator of the visualization scheme to the second value. Once the second visual indicator is assigned, the method further includes an eighth step 90 of updating the marker generated in generating step 84 to include the second visual indicator.

The method may further allow for the user or clinician of the system to enter or provide instructions relating to, for example, the particular ablation description parameter(s) or position signal metric(s) to be monitored, and the visualization scheme that is associated with the monitored ablation description parameter(s) or position signal metric(s). These instructions may be entered using, for example, the GUI 64, or the input device 69 associated therewith. In such an embodiment, the method further includes a step 92 of receiving at least one input signal representative of a user selection of at least one of an ablation description parameter or position signal metric of interest, and a visualization scheme to be associated with the ablation description parameter or position signal metric being monitored. In an embodiment wherein the input signal is representative of a user selection of a visualization scheme, the method further includes the step 94 of associating the selected visualization scheme with the monitored parameter/metric.

In an exemplary embodiment, the method further comprises a step 96 of determining the location in the tissue 12 that the acquired value corresponds to based on a position of the positioning electrode 42. In such an embodiment, the method further includes a step 98 of correlating the acquired value of the ablation description parameter or position signal metric with the location in the tissue 12. The method may further include a step 100 of superimposing the marker 68 generated in the generating step 84 onto a portion of the image or model 66 of the tissue 12 that corresponds to the location determined in the location determining step 96. The method may still further include a step 102 of displaying the image or model 66 with the marker 68 disposed thereon on the display device 24.

In an exemplary embodiment, in addition to characterizing the marker 68 and, in certain embodiments, placing the marker 68 onto an image 66 of the tissue 12, the method further comprises a step 104 of assessing the stability of the positioning electrode 42. The stability may be assessed based on predetermined stability criteria and using techniques described in greater detail above and as illustrated in FIGS. 11a-11c. In an exemplary embodiment wherein the stability of the positioning electrode 42, and therefore, the catheter 16 is assessed, the superimposing step 100 comprises superimposing the marker 68 onto the image 66 when the positioning electrode 42 meets the predetermined stability criteria. In another exemplary embodiment, rather than generating the marker 68 and superimposing it onto the image or model 66 when the electrode 42 is deemed stable, the method may alternatively include the step of obtaining a previously generated marker 68 and then superimposing it onto the image or model 66 when the electrode 42 is deemed to be stable. Accordingly, marker 68 may be acquired in a number of ways and then superimposed onto the image or model 66. In another exemplary embodiment, the acquiring step 78 comprises acquiring the value of the ablation description parameter or position signal metric when the positioning electrode 42 meets the predetermined stability criteria. Accordingly, the stability of the electrode 42, and therefore, the catheter 16, can be taken into consideration in a number of ways and at a number of stages in the methodology.

In an exemplary embodiment, the method may further include combining adjacent markers 68 together to form a single, contiguous marker 68. For example and with reference to FIG. 9, in one such embodiment, the method further includes a step 106 of determining whether any preexisting markers 68 are disposed within a predetermined distance (i.e., a spatial combining threshold) of the location determined in the determining step 96. If there are, the generating step 84 includes combining the generated marker corresponding to the location with the preexisting markers disposed within the predetermined distance. The ECU 22 may be preprogrammed with predetermined distance, or, as described above, the predetermined distance may be defined by the clinician.

In another exemplary embodiment, and as described in greater detail above, motion occurring as a result of one or more cyclic body activities may be taken into account and compensated for. For example, in an exemplary embodiment, the method includes a step 108 of taking into account and compensating for motion caused by a cyclic body activity. In one exemplary embodiment, the step 108 comprises the substeps of monitoring a cyclic body activity, such as, for example, respiration or cardiac activity, associating the position of the positioning electrode 42 corresponding to the location determined in determining step 96 and the value acquired in acquiring step 78 with a respective phase of the cyclic body activity. Once the association is made, the displaying step 102 comprises displaying the image or model 66 with the marker 68 disposed thereon during the appropriate phase of the cyclic body activity.

Figure 12:
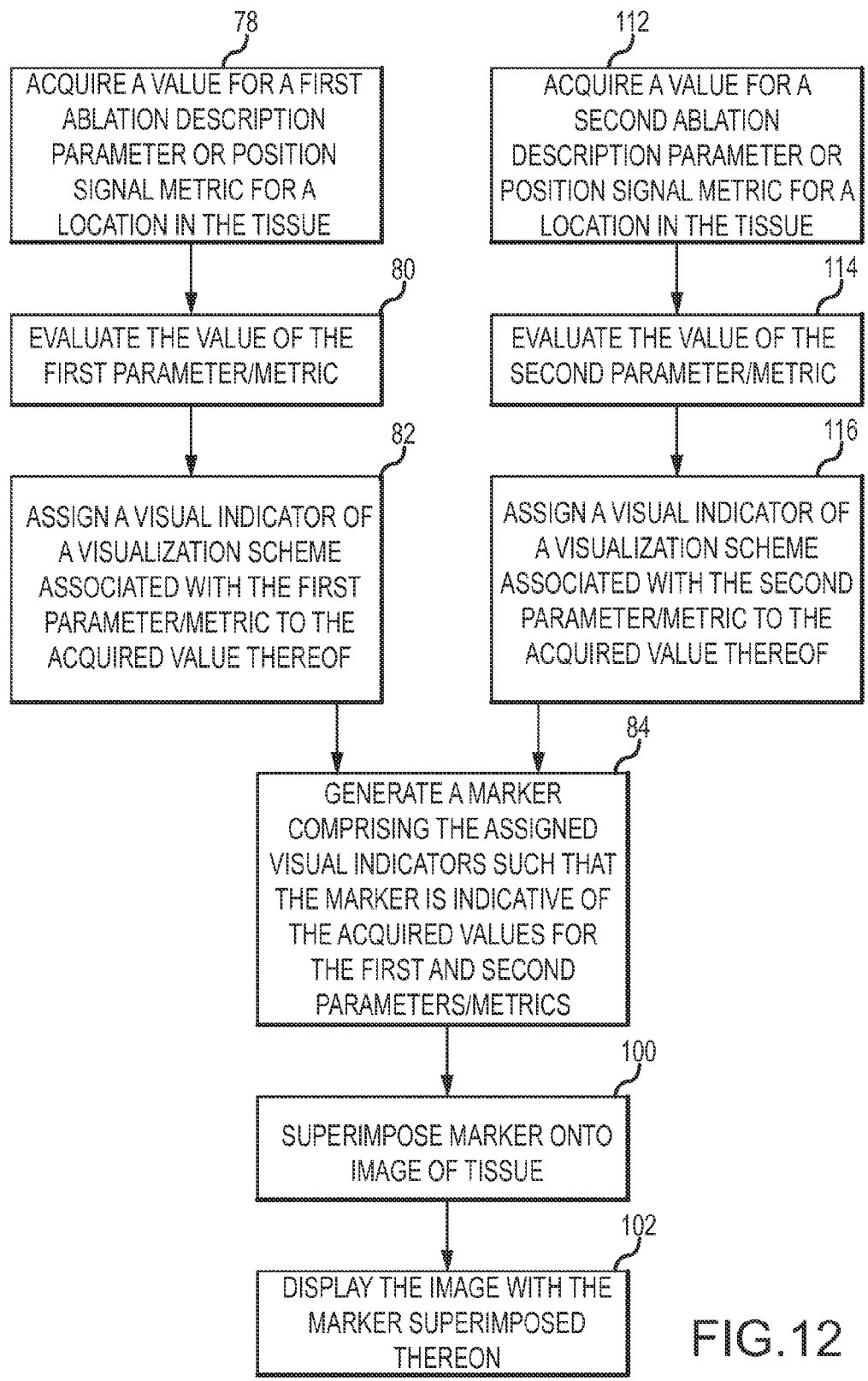
FIG. 12 is a flow chart illustrative of another exemplary embodiment of a method for presenting information relating to lesion formation in tissue in accordance with the present teachings.

In yet another exemplary embodiment illustrated, for example, in FIG. 12, more than one ablation description parameter or position signal metric may be used to characterize the marker 68. Accordingly, in one such embodiment, the parameter/metric corresponding to the value acquired in acquiring step 78 is a first parameter/metric, and the visualization scheme associated with this parameter/metric is a first visualization scheme. In such an embodiment, the method further includes a step 112 of acquiring a value for a second ablation description parameter or position signal metric, and a step 114 of evaluating the value of the second parameter/metric. The method further comprises a step 116 of assigning a visual indicator of a second visualization scheme associated with the second parameter/metric to the value acquired in the acquiring step 112. In this embodiment, the generating step 84 includes generating the marker 84 responsive to the evaluation of the values of the first and second parameters/metrics and the assignment of respective visual indicators, and the generated marker 68 comprises the respective visual indicators such that the marker 68 is indicative of the values of the first and second parameters/metrics. Alternatively, in another exemplary embodiment, a visual indicator may be assigned based on the combination of the values of the first and second parameters/metrics.

It will be appreciated that additional functionality described in greater detail above with respect to the system 10 may also be part of the inventive methodology. Therefore, to the extent such functionality has not been expressly described with respect to the methodology, the description thereof is incorporated herein by reference.

It should be understood that the system 10, and particularly the ECU 22, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms electrically connected and in communication are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

What is claimed is:

1. A system for presenting information representative of lesion formation in tissue during an ablation procedure, comprising:
an electronic control unit (ECU) configured to:
acquire a value for at least one of an ablation description parameter and a position signal metric, the value corresponding to a location in said tissue;
evaluate said value;
assign a visual indicator of a visualization scheme associated with said at least one of said ablation description parameter and said position signal metric to said value in response to the evaluation of said value;
generate a marker responsive to the evaluation of said value and assignment of said visual indicator, said marker comprising said visual indicator such that said marker is indicative of said value of said at least one of said ablation description parameter and said position signal metric;
determine said location in said tissue based on a position of a positioning sensor;
correlate said value of said at least one of said ablation description parameter and said position signal metric with said location in said tissue;
superimpose said marker onto a portion of an image or model of said tissue corresponding to said location in said tissue;

control a display device to display said image or model with said marker superimposed thereon;
determine if any preexisting markers are disposed within a predetermined distance of said location; and
generate a marker that combines said generated marker for said location with said preexisting markers disposed within said predetermined distance.

2. The system of claim 1, wherein said position signal metric is representative of the stability of said positioning sensor.

3. The system of claim 1, further comprising a user input device electrically coupled to said ECU, said user input device configured to allow a user to select said at least one of said ablation description parameter and said position signal metric from a plurality of ablation description parameters and at least one position signal metric, and to select said visualization scheme from a plurality of visualization schemes.

4. The system of claim 1, wherein said ECU is further configured to:
assess the stability of said positioning electrode based on predetermined stability criteria; and
control said display device to superimpose said marker responsive to a determination by said ECU that said positioning electrode meets said predetermined stability criteria.

5. The system of claim 1, wherein said ECU is further configured to:
assess the stability of said positioning electrode based on predetermined stability criteria; and
acquire said value of said at least one ablation description parameter and said position signal metric responsive to a determination by said ECU that said positioning electrode meets said predetermined stability criteria.

6. The system of claim 1, wherein said generated marker comprises a visual indicator corresponding to areas of overlap between each of said generated marker for said location and said preexisting markers, wherein said visual indicator corresponding to overlapping areas is different than that of non-overlapping areas.

7. The system of claim 1, wherein said ECU is further configured to:
monitor a cyclic body activity;
associate said position of said positioning sensor corresponding to said location and said acquired value of said at least one ablation description parameter and position signal metric corresponding to said location with a respective phase of said cyclic body activity; and
control said display device to display said image or model with said marker superimposed thereon during said phase of said cyclic body activity.

8. The system of claim 1, wherein said value is a value of a first ablation description parameter or position signal metric, said ECU further configured to:
acquire a value for a second ablation description parameter or position signal metric that is different from said first ablation description parameter or position signal metric;
evaluate said value of said second ablation description parameter or position signal metric;
assign said visual indicator based on a combination of said values of said first ablation description parameter or position signal metric and said second ablation description parameter or position signal metric; and
generate said marker responsive to the evaluation of said values of said first ablation description parameter or position signal metric and said second ablation description parameter or position signal metric.

9. The system of claim 1, wherein said value is a value of a first ablation description parameter or position signal metric, said ECU further configured to:
acquire a value for a second ablation description parameter or position signal metric that is different from said first ablation description parameter or position signal metric;
evaluate said value of said second ablation description parameter or position signal metric;
assign a visual indicator corresponding to said second ablation description parameter or position signal metric to said value in response to the evaluation of said value; and
generate said marker responsive to the evaluation of said values of said first ablation description parameter or position signal metric and said second ablation description parameter or position signal metric, said marker comprising said visual indicators of said values of said first ablation description parameter or position signal metric and said second ablation description parameter or position signal metric.

10. The system of claim 1, wherein said value is a value of an ablation description parameter and said visual indicator is a first visual indicator associated with a first visualization scheme, said ECU further configured to:
acquire a value for a position signal metric;
evaluate said value of said position signal metric;
assign a second visual indicator associated with a second visualization scheme that is different from said first visualization scheme to said value of said position signal metric in response to the evaluation of said value of said position signal metric; and
generate said marker responsive to the evaluation of said values of said ablation description parameter and said position signal metric, said marker comprising said first and second visual indicators such that said marker is indicative of said values of said ablation description parameter and said position signal metric.

11. The system of claim 1, wherein said ablation description parameter comprises a parameter of at least one of:
the power delivered to said tissue during said ablation procedure;
a temperature at an ablation electrode used in said ablation procedure;
an impedance of said tissue;
a detected voltage amplitude;
a degree of contact between a medical device and said tissue;
a proximity of a medical device and said tissue;
an index representative of lesion formation in said tissue;
a likelihood of barotrauma occurring in said tissue;
a predicted lesion depth;
a likelihood of a lesion achieving a predetermined depth;
a predicted temperature of said tissue; and
an intracardiac echocardiograph characteristic.

12. The system of claim 1, wherein said position signal metric comprises one of:
a value of a displacement between two positions of a positioning sensor over a predetermined period of time;
a percentage of displacements between a plurality of positions of a positioning sensor over a predetermined period of time that are within a predetermined radius; and
a stability index.

13. The system of claim 1, wherein said ablation description parameter comprises a parameter of a characteristic monitored by a visualization, navigation, and/or mapping system.

14. The system of claim 13, wherein said characteristic comprises an electrogram.

15. A method for presenting information representative of lesion formation in tissue during an ablation procedure, comprising the steps of:
- acquiring a value for at least one of an ablation description parameter and a position signal metric, said value corresponding to a location in said tissue;
- evaluating said value;
- assigning a visual indicator of a visualization scheme associated with said at least one of said ablation description parameter and said position signal metric to said value;
- generating a marker responsive to said evaluation of said value and assignment of said visual indicator, said marker comprising said visual indicator such that said marker is indicative of said value of said at least one of said ablation description parameter and said position signal metric;
- determining said location in said tissue based on a position of a positioning sensor;
- correlating said value of said at least one of said ablation description parameter and said position signal metric with said location in said tissue;
- superimposing said marker onto a portion of an image or model of said tissue corresponding to said location in said tissue;
- displaying said image or model with said marker superimposed thereon;
- determining if any preexisting markers are disposed within a predetermined distance of said location; and
- generating a marker that combines said generated marker for said location with said preexisting markers disposed within said predetermined distance.

16. The method of claim 15, wherein said value is a first value, said method further comprising:
- acquiring a second value of said at least one of said ablation description parameter and said position signal metric;
- evaluating said second value;
- wherein the step of assigning said visual indicator comprises assigning said visual indicator of said visualization scheme base on said first and second values.

17. The method of claim 15, further comprising the step of receiving at least one input signal representative of a user selection of at least one of said visualization scheme and said at least one of said ablation description parameter and position signal metric.

18. The method of claim 17, wherein said at least one input signal is representative of a user selection of a visualization scheme, said method further comprises the step of associating, in response to said at least one input signal, said visualization scheme with said at least one of said ablation description parameter and position signal metric corresponding to said acquired value.

19. The method of claim 15, said method further comprising the step of:
- assessing the stability of said positioning sensor based on predetermined stability criteria, and wherein said superimposing step comprises superimposing said marker when said positioning sensor meets said predetermined stability criteria.

20. The method of claim 15, said method further comprising the step of:
- assessing the stability of said positioning sensor based on predetermined stability criteria, and wherein said acquiring step comprises acquiring said value when said positioning sensor meets said predetermined stability criteria.

21. A system for presenting information representative of lesion formation in tissue during an ablation procedure, comprising:
- an electronic control unit (ECU) configured to:
  - acquire a position of a positioning sensor associated with a medical device;
  - determine a location in said tissue corresponding to said position of said positioning sensor;
  - assess the stability of said positioning sensor based on said position of said positioning sensor and predetermined stability criteria;
  - acquire a marker indicative of a value of at least one of an ablation description parameter corresponding to said location in said tissue, and a position signal metric corresponding to said location in said tissue and derived from said position of said positioning sensor; and
  - superimpose said marker onto a portion of an image or model of said tissue corresponding to said location in said tissue only after said positioning sensor meets said predetermined stability criteria.

22. The system of claim 21, wherein said value is a value of an ablation description parameter, said ECU further configured to:
- acquire a value for a position signal metric;
- evaluate said value of said position signal metric; and
- generate said marker responsive to the evaluation of said values of said ablation description parameter and said position signal metric such that said marker is indicative of said values of said ablation description parameter and said position signal metric.

23. The system of claim 22, said marker comprising:
- a first visual indicator associated with a first visualization scheme and indicative of said value of an ablation description parameter; and
- a second visual indicator associated with a second visualization scheme and indicative of said value of a position signal metric.

24. A method of presenting information representative of lesion formation in tissue during an ablation procedure, comprising:
- acquiring a position of a positioning sensor associated with a medical device;
- determining a location in said tissue corresponding to said position of said positioning sensor;
- assessing the stability of said positioning sensor based on said position of said positioning sensor and predetermined stability criteria;
- acquiring a marker indicative of a value of at least one of an ablation description parameter corresponding to said location in said tissue, and a position signal metric corresponding to said location in said tissue and derived from said position of said positioning sensor; and
- superimposing said marker onto a portion of an image or model of said tissue corresponding to said location in said tissue only after said positioning sensor meets said predetermined stability criteria.

25. The method of claim 24, wherein said value is a value of an ablation description parameter, the method further comprising:
- acquiring a value for a position signal metric;
- evaluating said value of said position signal metric; and
- generating said marker responsive to the evaluation of said values of said ablation description parameter and said position signal metric such that said marker is indicative of said values of said ablation description parameter and said position signal metric.

26. The method of claim 25, said marker comprising:
- a first visual indicator associated with a first visualization scheme and indicative of said value of an ablation description parameter; and
- a second visual indicator associated with a second visualization scheme and indicative of said value of a position signal metric.

* * * * *